United States Patent
Holmeide et al.

(10) Patent No.: US 8,759,558 B2
(45) Date of Patent: Jun. 24, 2014

(54) SULPHUR CONTAINING LIPIDS FOR USE AS FOOD SUPPLEMENT OR AS MEDICAMENT

(75) Inventors: Anne Kristin Holmeide, Olso (NO); Ragnar Hovland, Nesoddtangen (NO); Morten Brændvang, Sandefjord (NO)

(73) Assignee: Pronova Biopharma Norge AS, Lysaker (NO)

( * ) Notice: Subject to any disclaimer, the term of this patent is extended or adjusted under 35 U.S.C. 154(b) by 517 days.

(21) Appl. No.: 13/054,212

(22) PCT Filed: Jul. 13, 2009

(86) PCT No.: PCT/NO2009/000262
§ 371 (c)(1),
(2), (4) Date: Apr. 13, 2011

(87) PCT Pub. No.: WO2010/008299
PCT Pub. Date: Jan. 21, 2010

(65) Prior Publication Data
US 2011/0190395 A1    Aug. 4, 2011

Related U.S. Application Data

(60) Provisional application No. 61/080,804, filed on Jul. 15, 2008.

(30) Foreign Application Priority Data

Jul. 15, 2008   (EP) .................................... 08160450

(51) Int. Cl.
*C11D 1/28*   (2006.01)
*A61K 31/10*  (2006.01)

(52) U.S. Cl.
USPC ............. 554/85; 554/88; 554/101; 514/710; 514/706; 514/708; 514/709; 514/550

(58) Field of Classification Search
None
See application file for complete search history.

(56) References Cited

U.S. PATENT DOCUMENTS

| 2,909,554 A | 10/1959 | Doerr |
| 4,009,211 A | 2/1977 | Onopchenko et al. |

(Continued)

FOREIGN PATENT DOCUMENTS

| CA | 2115345 | * | 2/1993 | ............ C07C 323/41 |
| CN | 101225064 A | | 7/2008 | |

(Continued)

OTHER PUBLICATIONS

Hill, A.J. et al., Some alpha-alkylthio aliphatic acids, 1943, Journal of the American Chemical Society, vol. 65, No. 12, pp. 2330-2301.*

(Continued)

*Primary Examiner* — Yate K Cutliff
(74) *Attorney, Agent, or Firm* — Finnegan, Henderson, Farabow, Garrett & Dunner LLP

(57) ABSTRACT

The present invention relates to lipid compounds of the general formula (I):

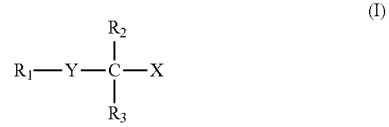

(I)

wherein $R_1$ is selected from a $C_{10}$-$C_{22}$ alkyl, a $C_{10}$-$C_{22}$ alkenyl having 1-6 double bonds, and a $C_{10}$-$C_{22}$ alkynyl having 1-6 triple bonds; $R_2$ and $R_3$ are the same or different and may be selected from a group of different substituents; Y is selected from sulphur, sulfoxide, and sulfone; and X represents a carboxylic acid or a derivative thereof, a carboxylic ester, a carboxylic anhydride or a carboxamide; or a pharmaceutically acceptable salt, complex or solvate thereof.

The invention also relates to pharmaceutical compositions and lipid compositions comprising such compounds, and to such compounds for use as medicaments or for use in therapy, in particular for the treatment of diseases related to the cardiovascular, metabolic and inflammatory disease area.

71 Claims, 6 Drawing Sheets

(56) References Cited

U.S. PATENT DOCUMENTS

| | | | |
|---|---|---|---|
| 4,032,564 | A | 6/1977 | Henrick et al. |
| 4,040,781 | A | 8/1977 | Lamberti et al. |
| 4,209,410 | A | 6/1980 | Baldwin |
| 4,214,088 | A | 7/1980 | Abeler et al. |
| 4,286,053 | A | 8/1981 | Ishikawa et al. |
| 4,297,268 | A | 10/1981 | Abeler et al. |
| 4,368,190 | A | 1/1983 | Shen et al. |
| 4,411,808 | A | 10/1983 | Gutierrez et al. |
| 4,444,766 | A | 4/1984 | Bosies et al. |
| 5,306,754 | A | 4/1994 | Yamamoto et al. |
| 5,328,952 | A | 7/1994 | Brodnyan et al. |
| 5,447,820 | A | 9/1995 | Hayakawa et al. |
| 5,612,093 | A | 3/1997 | Braig et al. |
| 5,763,517 | A | 6/1998 | Yamamoto et al. |
| 5,770,584 | A | 6/1998 | Kucera et al. |
| 5,990,173 | A | 11/1999 | Patoiseau et al. |
| 6,060,515 | A | 5/2000 | Bass et al. |
| 6,365,628 | B1 * | 4/2002 | Berge ............... 514/546 |
| 6,376,688 | B1 * | 4/2002 | Ferrante et al. ........... 554/101 |
| 6,511,670 | B1 | 1/2003 | Maignan et al. |
| 6,624,190 | B2 | 9/2003 | Khoury et al. |
| 6,723,717 | B1 | 4/2004 | Youngquist et al. |
| 7,250,456 | B2 | 7/2007 | Eigen et al. |
| 7,273,852 | B2 | 9/2007 | Tsuji et al. |
| 7,427,583 | B2 | 9/2008 | Couillet et al. |
| 7,517,858 | B1 | 4/2009 | Hostetler et al. |
| 7,902,399 | B2 | 3/2011 | Berge et al. |
| 7,968,617 | B2 | 6/2011 | Thalacker et al. |
| 8,304,551 | B2 | 11/2012 | Milne et al. |
| 2003/0147814 | A1 | 8/2003 | Scherrer et al. |
| 2004/0126424 | A1 | 7/2004 | Jandacek et al. |
| 2005/0107503 | A1 | 5/2005 | Couillet et al. |
| 2006/0247458 | A1 | 11/2006 | Yamamoto et al. |
| 2007/0060497 | A1 | 3/2007 | Krahmer et al. |
| 2007/0254862 | A1 | 11/2007 | Antel et al. |
| 2009/0137567 | A1 | 5/2009 | Perrine et al. |
| 2010/0280109 | A1 * | 11/2010 | Holmeide ............... 514/546 |
| 2011/0190395 | A1 | 8/2011 | Holmeide et al. |
| 2012/0122940 | A1 | 5/2012 | Hovland et al. |
| 2012/0252850 | A1 | 10/2012 | Milne et al. |
| 2012/0264791 | A1 | 10/2012 | Milne et al. |
| 2013/0046013 | A1 | 2/2013 | Hovland et al. |

FOREIGN PATENT DOCUMENTS

| | | |
|---|---|---|
| EP | 0 002 007 | 5/1979 |
| EP | 0 050 327 | 4/1982 |
| EP | 0 175 591 | 3/1986 |
| EP | 0 399 183 A1 | 11/1990 |
| EP | 0 463 947 | 1/1992 |
| GB | 1038723 | 8/1966 |
| GB | 1523276 | 8/1978 |
| JP | 04-051149 A | 2/1992 |
| WO | WO97/38688 | 10/1997 |
| WO | WO00/72920 | 12/2000 |
| WO | WO01/98328 | 12/2001 |
| WO | WO03/014073 | 2/2003 |
| WO | WO2005/073164 | 8/2005 |
| WO | WO2006/025246 | 3/2006 |
| WO | WO2006/094915 | 9/2006 |
| WO | WO2007/116027 | 10/2007 |
| WO | WO 2008/053331 A1 | 5/2008 |
| WO | WO2008/053340 | 5/2008 |
| WO | WO2008/125241 | 10/2008 |
| WO | WO 2009/061208 A1 | 5/2009 |
| WO | WO2009/149496 | 12/2009 |
| WO | WO2009/156621 | 12/2009 |
| WO | WO2010/006085 | 1/2010 |
| WO | WO2010/008299 | 1/2010 |
| WO | WO2010/128401 | 11/2010 |
| WO | WO2011/089529 | 7/2011 |
| WO | WO2012/059818 | 5/2012 |
| WO | WO2012/115695 | 8/2012 |
| WO | WO2013/016531 | 1/2013 |

OTHER PUBLICATIONS

Silverman, R.B., The organic chemistry of drug designa nd drug action, 1992, Academic Press, (20 pages).*
International Search Report for PCT/NO2009/000262 dated Oct. 23, 2009 (9 pages).
Jones, P.B. et al., "A new class of antituberculosis agents," *J. Med. Chem.* (2000) vol. 43, pp. 3304-3314.
Lamango, N.S. et al., "Inhibition mechanism of S-adenosylmethionine-induced movement deficits by prenylcysteine analogs," *Pharmacology, Biochemistry, and Behavior* (2003) vol. 76, pp. 433-442.
Larsen, N.L. et al., "Sulfur substituted and α-methylated fatty acids as peroxisome proliferator-activated receptor activators," *Lipids* (2005) vol. 40, pp. 49-57.
Vaagenes, H. et al., "Methylated eicosapentaenoic acid and tetradecylathioacetic acid: Effects on fatty acid metabolism," *Biochemical Pharmacology* (1999) vol. 58, pp. 1133-1143.
Ahmad, J. et al., "Reactions in Monolayers: Base-Catalyzed Ester Hydrolysis Revisited," *Langmuir* (1990) 6:1797-1799.
Copending U.S. Appl. No. 12/741,890, filed Jul. 27, 2011.
Copending U.S. Appl. No. 13/319,101, filed Jan. 24, 2012.
Copending U.S. Appl. No. 13/574,132, filed Jul. 19, 2012.
Copending U.S. Appl. No. 13/883,405, filed May 3, 2013.
Derzhinskii, A.R. et al., "Functional Sulfur-Containing Compounds. Part 4. Preparation of Chloro(Bromo)Alkyl Sulfones by Oxidative Halogenation of Hydroxyalkyl Sulfides and Sulfoxides with Mixtures of Hydrogen Peroxide and a Hydrohalic Acid," *Izvestiya Akademii Nauk SSSR, Seriya Khimicheskaya* (1982) 31(5):995-1001.
English language abstract for EP 0 463 947, Autochem, 1992.
Ferrell, W.J., "Synthesis and Properties of 35S, 14C and 3H Labeled S-Alkyl Glycerol Ethers and Derivatives," *Chemistry and Physics of Lipids* (1976) 16:276-284.
Ferrucci, L. et al., "Relationship of Plasma Polyunsaturated Fatty Acids to Circulating Inflammatory Markers," *J. Clin. Endocrin. & Metab.* (2006) 91(2):439-446.
Geleijnse, J.M. et al., "Blood Pressure Response to Fish Oil Supplementation: Metaregression Analysis of Randomized Trials," *J. Hypertension* (2002) 20(8):1493-1499.
Goldsworthy, L.J. et al., "Some Sulphides Containing the 2-Chloroethyl Group," *J. Chem. Soc.* (1948) 2177-2179.
Grupp, I.L. et al., "Protection Against Hypoxia-Reoxygenation in the Absence of Poly (ADP-Ribose) Synthetase in Isolated Working Hearts," *J. Mol. Cell Cardiol.* (1999) 31:297-303.
Hermetter, A. & Paltauf, F., "A Facile Procedure for the Synthesis of Saturated Phosphatidylcholines," *Chemistry & Physics of Lipids* (1981) 28:111-115.
Holmeide, A.K. & Skattebol, L., "Syntheses of Some Polyunsaturated Trifluoromethyl Ketones as Potential Phospholipase A2 Inhibitors," *J. Chem. Soc., Perkin Trans.* (2000) 1:2271-2276.
Hosokawa, M. et al., "Preparation of Therapeutic Phospholipids Through Porcine Pancreatic Phospholipase A2-Mediated Esterification and Lipozyme-Mediated Acidolysis," *J. Am. Oil Chem. Soc.* (1995) 72(11):1287-1291.
International Search Report for International Application No. PCT/IB2010/001251, dated Oct. 4, 2010.
International Search Report for International Application No. PCT/IB2011/000250, dated May 31, 2011.
International Search Report for International Application No. PCT/NO2008/000391, dated Feb. 4, 2009.
Kasai, Y. et al., "Synthesis of Diphenylalkane Sulfonate and Its Surface Activity," *J. Chem. Soc. Japan* (1965) 68(11):2073-2077.
Larsen, L.N. et al., "α- and β-Alkyl-Substituted Eicosapentaenoic Acids: Incorporation into Phospholipids and Effects on Prostaglandin H Synthase and 5-Lipoxygenase," *Biochemical Pharmacology* (1998) 55:405-11.
Lilja-Hallberg, M. & Harrod, M., "Enzymatic Esterification of Long Polyunsaturated Fatty Acids and Lyso-Phosphatidylcholine in Isooctane and Ethanol," *Biocatalysis* (1994) 9:195-207.
Livingston, J.R. & Drogin, R., "The Synthesis and Some Surface Active Properties of Alkylthioalkyl and Alkoxyalkyl Sulfates," *J. Am. Oil Chem. Soc.* (1965) 42:720-723.

(56) References Cited

OTHER PUBLICATIONS

Masson, M. et al., "Marine Lipids for Prodrugs, Soft Compounds and Other Pharmaceutical Applications," Pharmazie (2000) 55(3):172-177.

Office Action dated Apr. 24, 2013, from U.S. Appl. No. 13/319,101.

Office Action dated Aug. 3, 2012, from U.S. Appl. No. 12/741,890.

Office Action dated Aug. 6, 2013, from U.S. Appl. No. 12/741,890.

Office Action dated Dec. 10, 2012, from U.S. Appl. No. 12/741,890.

Office Action dated Jan. 31, 2013, from U.S. Appl. No. 13/319,101.

Okoronkwo, A.E. et al., "Synthesis of ω-Hydroxy-α-Alkyl/Aryl-γ-Organo-Selenium and γ-Organo-Tellurium: A New Class of Organochalcogen Compounds with Antinociceptive Activity," Tetrahedron Letters (2008) 49:3252-3256.

Parkkari, T. et al., "α-Methylated Derivatives of 2-Arachidonoyl Glycerol: Synthesis, CB1 Receptor Activity, and Enzymatic Stability," Bioorg. & Med. Chem. Letters (2006) 16:2437-2440.

Pitt, M.J. et al., "Synthesis of Polyunsaturated β-Oxa Fatty Acids via Rhodium Mediated Carbenoid Insertion," Synthesis (1997) 7:1240-42.

Registry Copyright 2008 ACS on STN (RN 785712-42-7, 714185-72-5, 45247-37-8).

Rossmeisl, M. et al., "Prevention and Reversal of Obesity and Glucose Intolerance in Mice by DHA Derivatives," Obesity (2009) 17(5):1023-1031.

Shchepin, R. et al., "Quorum Sensing in *Candida albicans*: Probing Farnesol's Mode of Action with 40 Natural and Synthetic Farnesol Analogs," (2003) Chemistry & Biology 10:743-750.

Shirley, D.A. et al., "Alkylation with Long Chain ρ-Toluenesulfonates. IV. Alkylation of Alcohols and Amines with n-Octadecyl ρ-Toluenesulfonate," J. Org. Chem. (1953) 18:378-381.

Simopoulos, A.P., "Essential Fatty Acids in Health and Chronic Disease," Am. J. Clin. Nutr. (1999) 70(Suppl):560S-569S.

Srisiri, W. et al., "Syntheses of Polymerizable Monoacylglycerols and 1,2-Diacyl-sn-Glycerols," J. Org. Chem. (1996) 61(16):5911-5915.

Storlien, L.H. et al., "Polyunsaturated Fatty Acids, Membrane Function and Metabolic Diseases Such As Diabetes and Obesity," Curr. Opin. Clin. Nutr. & Metab. Care (1998) 1(6):559-563.

Tran, P.O.T. et al., "Inhibition of Interleukin-1β-Induced COX-2 and EP3 Gene Expression by Sodium Salicylate Enhances Pancreatic Islet β-Cell Function," Diabetes (2002) 51:1772-78.

Wang, P. et al., "Synthesis of Phospholipid-Inhibitor Conjugates by Enzymatic Transphosphatidylation with Phospholipase D," J. Am. Chem. Soc. (1993) 115:10487-10491.

Willumsen, N. et al., "Enhanced Hepatic Fatty Acid Oxidation and Upregulated Carnitine Palmitoyltransferase II Gene Expression by Methyl 3-Thiaoctadeca-6,9,12,15-Tetraenoate in Rats," J. Lipid Mediators Cell Signalling (1997) 17:115-134.

Willumsen, N. et al., "On the Effect of 2-Deuterium- and 2-Methyl-Eicosapentaenoic Acid Derivatives on Triglycerides, Peroxisomal B-Oxidation and Platelet Aggregation in Rats," Biochimica et Biophysica Acta (1998) 1369:193-203.

Woodbury, D.M. & Fingle, E., "Drugs Effective in the Therapy of the Epilepsies," Basis of Therapeutics 201-26 (5th Ed. 1975).

Zeynalov, B.K., "Synthesis and Investigation of Esters of Alkyl Selenium Ethanols," Azerbaijan J. Chem. (1981) 5:41-43.

\* cited by examiner

SULPHUR CONTAINING LIPIDS FOR USE AS FOOD SUPPLEMENT OR AS MEDICAMENT

This application is a national stage filing under 35 U.S.C. §371 of International Application No. PCT/NO20009/000262 filed on Jul. 13, 2009. This International Application also claims the benefit of U.S. Provisional Application No. 61/080,804 filed on Jul. 15, 2008, and European Application No. 08160450.6 filed on Jul. 15, 2008. All of those applications are incorporated by reference herein in their entireties.

TECHNICAL FIELD

The present invention relates to lipid compounds of the general formula (I):

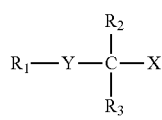

wherein
- $R_1$ is selected from a $C_{10}$-$C_{22}$ alkyl, a $C_{10}$-$C_{22}$ alkenyl having 1-6 double bonds, and a $C_{10}$-$C_{22}$ alkynyl having 1-6 triple bonds;
- $R_2$ and $R_3$ are the same or different and may be selected from a group of substituents consisting of a hydrogen atom, a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group, and an alkylamino group, provided that $R_2$ and $R_3$ cannot both be a hydrogen atom; or
- $R_2$ and $R_3$ can be connected in order to form a cycloalkane like cyclopropane, cyclobutane, cyclopentane or cyclohexane;
- Y is selected from sulphur, sulfoxide, and sulfone;
- X represents a carboxylic acid or a derivative thereof, a carboxylic ester or a carboxamide;

or a pharmaceutically acceptable salt, solvate, solvate of such salt or a prodrug thereof.

In those cases were $R_2$ and $R_3$ are different, the compounds of formula (I) are capable of existing in stereoisomeric forms. It will be understood that the invention encompasses all optical isomers of the compounds of formula (I) and mixtures thereof.

The invention also relates to pharmaceutical compositions and lipid compositions comprising such compounds, and to such compounds for use as medicaments or for use in therapy, in particular for the treatment of diseases related to the cardiovascular, metabolic and inflammatory disease area.

BACKGROUND OF THE INVENTION

Up to date, there has been a lot of research on fatty acid analogues and their effects on diverse physiological processes impacting normal health and chronic diseases.

For example, dietary polyunsaturated fatty acids (PUFAs) have been shown to regulate plasma lipid levels, cardiovascular and immune functions, insulin action, and neuronal development and visual function.

Tetradecylthioacetic acid (TTA) is a modified fatty acid which has a number of powerful effects demonstrable both in-vivo and in-vitro.

TTA has properties very similar to natural fatty acids, the main difference being that it cannot be oxidised by the mitochondrial β-oxidation, but significantly increases the oxidation of other fatty acids. Despite the fact that TTA is not able to undergo β-oxidation, it is metabolised in most ways as a normal saturated fatty acid.

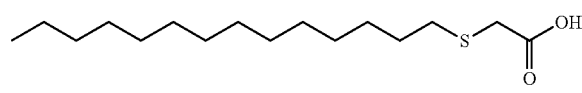

TTA

TTA affects oxidative status at different levels by having the potential of changing the antioxidant defence system, in addition to being an antioxidant itself through its free radical scavenging capacity.

Addition of TTA may prevent the oxidative modification of low-density lipoprotein (LDL) particles in plasma and reduce the generation of lipid peroxides.

Several polyunsaturated fatty acid derivatives with sulfur in 3-position have been prepared (Flock et al, Acta Chemica Scand., 1999, 53, 436). Methyl (all-Z)-3-thia-6,9,12,15-octadecatetraenoate was tested in a Wistar rat model, and the effects were compared to the effects of TTA. The results suggest that both the saturated and the unsaturated fatty acids lowered plasma triglycerides to a similar extent (Willumsen et al, J. Lipid Mediators Cell Signalling, 1997, 17, 115)

It has surprisingly been found that novel fatty acid derivatives represented by the general formula (I) have higher affinities for the receptors PPARα and PPARγ compared to TTA and (all-Z)-3-thia-6,9,12,15-octadecatetraenoic acid. Fatty acid derivatives represented by the general formula (I) also reduced triglyceride, cholesterol and free fatty acids levels in a dyslipidemic mice model to a greater extent than TTA and (all-Z)-3-thia-6,9,12,15-octadecatetraenoic acid.

SUMMARY OF THE INVENTION

Figure 1:
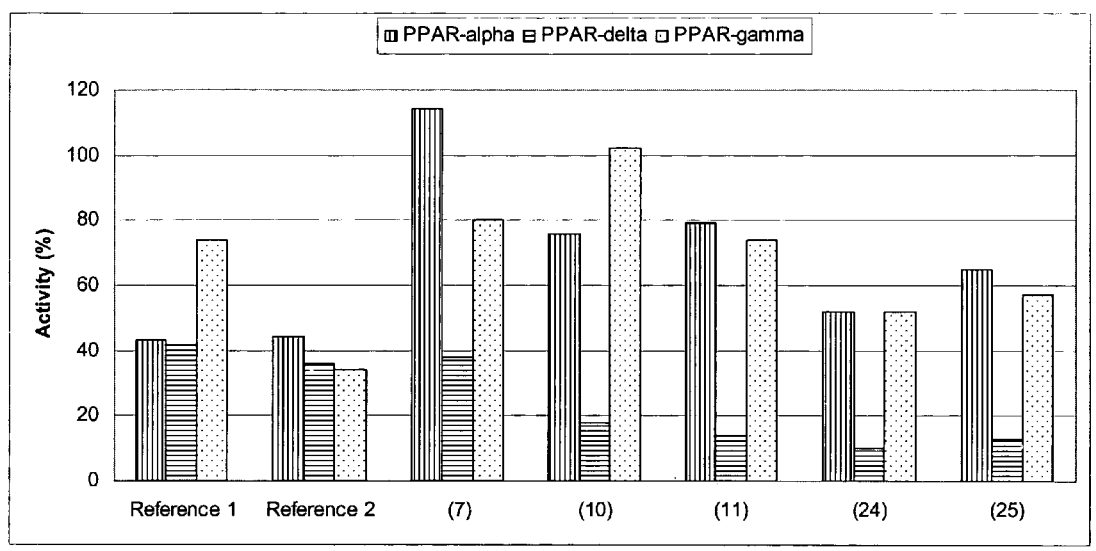
FIG. 1: Results of PPAR activation in PPARα, PPARδ, and PPARγ luciferase reporter cell lines by compounds according to the present disclosure compared to PPARβ, PPARδ, PPARγ activity of GW7647, L-165041, and BRL49653, respectively.

One object of the present invention is to provide lipid compounds having improved biological activity compared to 3-thia fatty acids. This object is achieved by a lipid compound of formula (I)

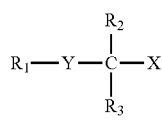

(I)

In particular, the present invention relates to compounds of formula (I), wherein:

$R_1$ is selected from a $C_{10}$-$C_{22}$ alkyl, a $C_{10}$-$C_{22}$ alkenyl having 1-6 double bonds, and a $C_{10}$-$C_{22}$ alkynyl having 1-6 triple bonds;

$R_2$ and $R_3$ are the same or different and may be selected from a group of substituents consisting of a hydrogen atom, a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group, and an alkylamino group, provided that $R_2$ and $R_3$ cannot both be a hydrogen atom; or $R_2$ and $R_3$ can be connected in order to form a cycloalkane like cyclopropane, cyclobutane, cyclopentane or cyclohexane;

Y is selected from sulphur, sulfoxide, and sulfone;

X represents a carboxylic acid or a derivative thereof, a carboxylic ester or a carboxamide;

or a pharmaceutically acceptable salt, solvate, solvate of such salt or a prodrug thereof.

In a compound according to the invention, said alkyl group may be selected from the group consisting of methyl, ethyl, n-propyl, isopropyl, n-butyl, sec.-butyl, and n-hexyl; said alkenyl group may be selected from the group consisting of allyl, 2-butenyl, and 3-hexenyl; said alkynyl group may be selected from the group consisting of propargyl, 2-butynyl, and 3-hexynyl; said halogen atom may be selected from the group consisting of fluorine, chlorine, bromine, and iodine; said alkoxy group may be selected from the group consisting of methoxy, ethoxy, propoxy, isopropoxy, sec.-butoxy, phenoxy, benzyloxy, $OCH_2CF_3$, and $OCH_2CH_2OCH_3$; said acyloxy group may be selected from acetoxy, propionoxy, and butyroxy; said aryl group is a phenyl group; said alkylthio group may be selected from the group consisting of methylthio, ethylthio, isopropylthio, and phenylthio; said alkoxycarbonyl group may be selected from the group consisting of methoxycarbonyl, ethoxycarbonyl, propoxycarbonyl, and butoxycarbonyl; said alkylsulfinyl group may be selected from the group consisting of methanesulfinyl, ethanesulfinyl, and isopropanesulfinyl; said alkylsulfonyl group may be selected from the group consisting of methanesulfonyl, ethanesulfonyl, and isopropanesulfonyl; said alkylamino group may be selected from the group consisting of methylamino, dimethylamino, ethylamino, and diethylamino; said carboxylate group may be selected from the group consisting of ethyl carboxylate, methyl carboxylate, n-propyl carboxylate, isopropyl carboxylate, n-butyl carboxylate, sec.-butyl carboxylate, and n-hexyl carboxylate; said carboxamide group may be selected from the group consisting of carboxamide such as N-methyl carboxamide, N,N-dimethyl carboxamide, N-ethyl carboxamide and N,N-diethyl carboxamide.

In one embodiment of the invention, one of the substituents $R_2$ and $R_3$ of the compound of formula (I) is hydrogen and the other one is selected from a group of substituents consisting of a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group, and an alkylamino group.

In a preferred embodiment $R_2$ and $R_3$ are independently selected from a hydrogen atom, an alkyl group, an alkoxy group or an aryl group; or $R_2$ and $R_3$ can be connected in order to form a cycloalkane.

In another preferred embodiment $R_2$ and $R_3$ are independently selected from a hydrogen atom, an alkyl group, or a methoxy group or an ethoxy group.

In yet another preferred embodiment $R_2$ and $R_3$ are independently selected from a hydrogen atom, an ethyl, methoxy or ethoxy group, phenyl; or $R_2$ and $R_3$ are connected to form a cyclobutane group.

In another embodiment of the invention, the substituents $R_2$ and $R_3$ of the compound of formula (I) are the same or different and may be selected from a group of substituents consisting of a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group. Preferably $R_2$ and $R_3$ are alkyl groups selected from methyl, ethyl, n-propyl, or isopropyl, more preferably selected from methyl or ethyl, and most preferably $R_2$ and $R_3$ are ethyl.

In one embodiment of the invention the substituent $R_1$ of the compound of formula (I) is a $C_{10}$-$C_{22}$ alkyl, and the said compound is derived from a saturated fatty acid.

Preferably, the substituents $R_2$ and $R_3$ of the compound of formula (I) are the same or different and may be selected from a group of substituents as mentioned above, and the substituent $R_1$ is a $C_{10}$-$C_{22}$ alkyl, and the said compound is derived from a saturated fatty acid.

When derived from a polyunsaturated fatty acid, $R_1$ is typically a $C_{10}$-$C_{22}$ alkenyl with 2-6 double bonds, e.g. 3-6 double bounds, e.g. 3-6 methylene interrupted double bonds in Z configuration. For example, $R_1$ is:

a $C_{15}$ alkenyl with 4 methylene interrupted double bonds in Z-configuration a $C_{18}$ alkenyl with 3-5 double bonds, e.g. a $C_{18}$ alkenyl with 5 methylene interrupted double bonds in Z configuration a $C_{14}$-$C_{22}$ alkenyl group with at least one double bond, having Z configuration, and having the first double bond at the third carbon-carbon bond from the omega ($\omega$) end of the carbon chain a $C_{20}$ alkenyl with 5 methylene interrupted double bonds in Z-configuration a $C_{22}$ alkenyl with 6 methylene interrupted double bonds in Z-configuration.

Furthermore, $R_1$ may be a $C_{10}$-$C_{22}$ alkynyl, e.g. a $C_{16}$-$C_{22}$ alkynyl with 1-6 triple bonds.

In one embodiment of the invention, the substituent Y of the compound of formula (I) is sulfur.

In another embodiment of the invention, the substituent Y of the compound of formula (I) is sulfoxide.

In still another embodiment of the invention, the substituent Y of the compound of formula (I) is sulfone.

In one embodiment of the invention, the substituent X of the compound of formula (I) is a carboxylic acid in the form of an ester, a free acid, a triglyceride or a phospholipid.

Preferably, the substituent X is a carboxylic acid in the form of an ester, or a free acid, and more preferably X is a carboxylic acid in the form of a free acid.

In another embodiment of the invention, the substituent $R_1$ is a $C_{10}$-$C_{22}$ alkyl, and the lipid compound being derived from a saturated fatty acid; $R_2$ and $R_3$ are the same or different and may be selected from a group of substituents consisting of a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group; preferably $R_2$ and $R_3$ are alkyl groups; and X is a carboxylic acid in the form of a free acid.

The invention also relates to salts of the compound of formula (I). Such salts may be represented by

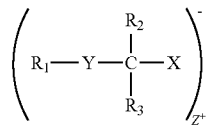

wherein X is COO$^-$, $Z^+$ is selected from the group consisting of Li$^+$, Na$^+$, K$^+$, NH$_4^+$,

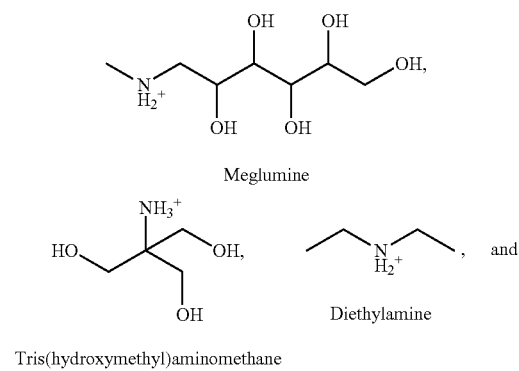

Meglumine

Tris(hydroxymethyl)aminomethane      Diethylamine

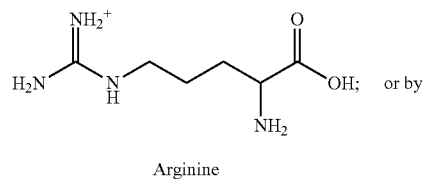

Arginine

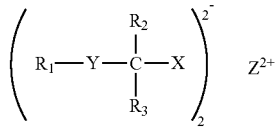

wherein X=COO$^-$, $Z^{2+}$ is selected from the group consisting of Mg$^{2+}$, Ca$^{2+}$,

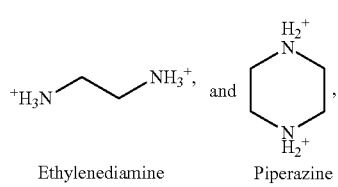

Ethylenediamine      Piperazine

Another representative salt is

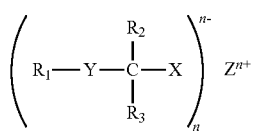

wherein X is COO$^-$, $Z^{n+}$ is a polyvalent cation such as

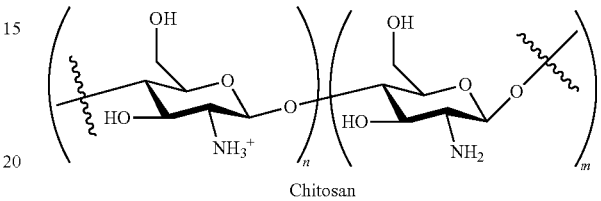

Chitosan

In the case the compounds of formula (I) is in the form of a phospholipid, such compounds may be represented by the following formulas (II-IV),

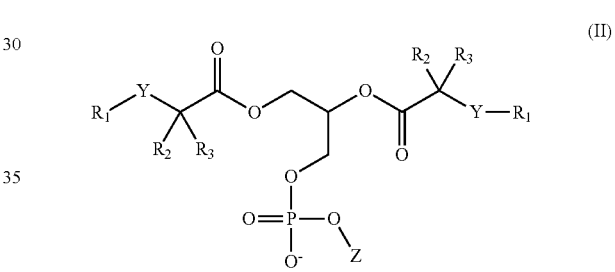

(II)

wherein Z is:

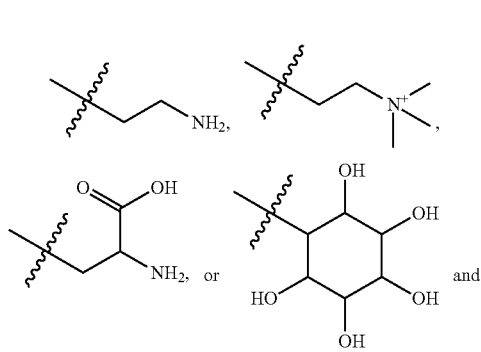

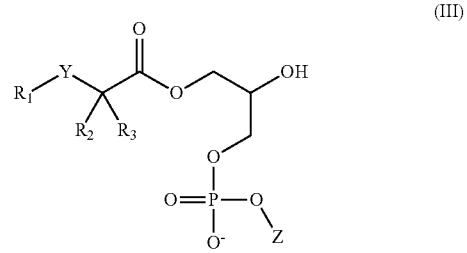

(III)

wherein Z is:

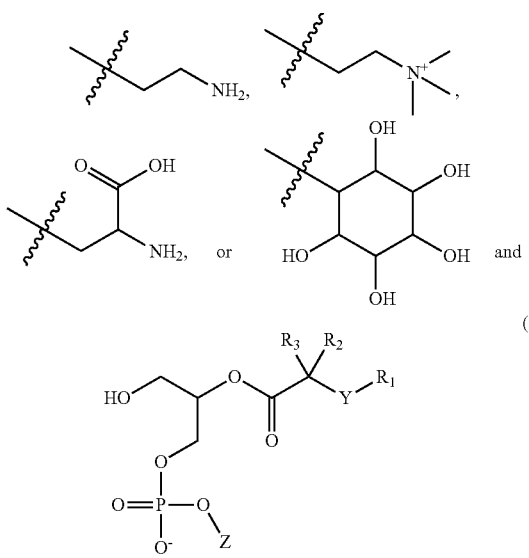

wherein Z is:

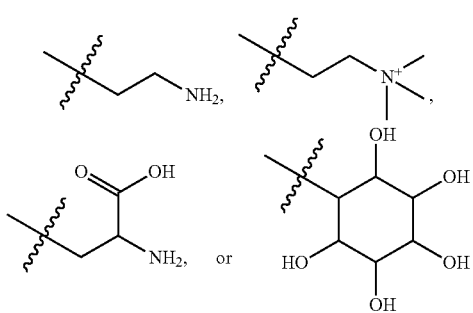

Compounds of formula (I), wherein X is a carboxylic acid in the form of a triglyceride, a 1,2-diglyceride, a 1,3 diglyceride, a 1-monoglyceride and a 2-monoglyceride, are also included in the present invention. These are hereinafter represented by the formulas (V), (VI), (VII), (VIII) and (IX), respectively.

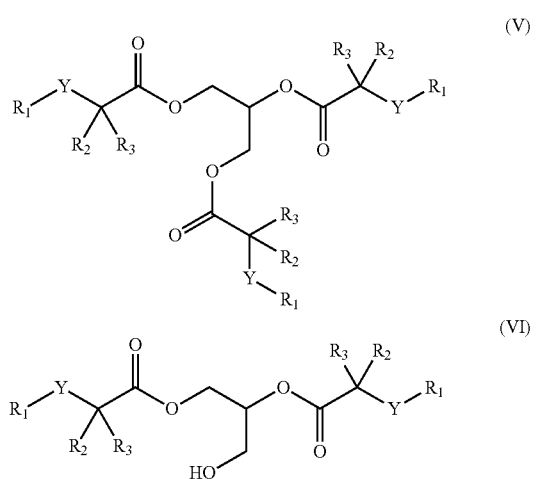

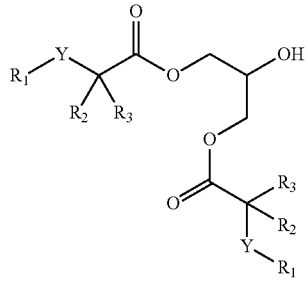

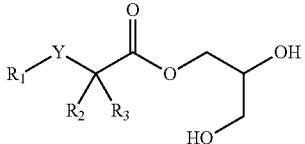

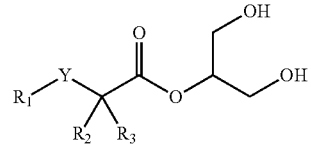

The compounds of formula (I) are capable of existing in stereoisomeric forms. It will be understood that the invention encompasses all optical isomers of the compounds of formula (I) and mixtures thereof. Hence, compounds of formula (I) being present as diastereomers, racemates and enantiomers are included.

In a preferred embodiment of the invention the compound of formula (I) is

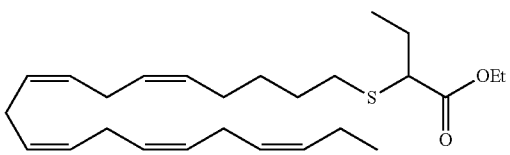 [SMILES: CC/C=C\C/C=C\C/C=C\C/C=C\C/C=C\CCCCSC(CC)C(=O)OCC]

ethyl 2-((5Z,8Z,11Z,14Z,17Z)-icosa-5,8,11,14,17-pentaenylthio)butanoate.

In another preferred embodiment of the invention the compound of formula (I) is

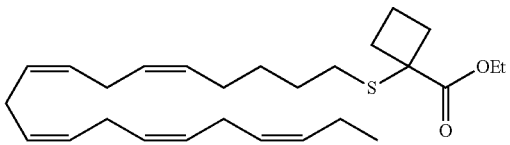 [SMILES: CC/C=C\C/C=C\C/C=C\C/C=C\C/C=C\CCCCSC1(C(=O)OCC)CCC1]

ethyl 1-((5Z,8Z,11Z,14Z,17Z)-icosa-5,8,11,14,17-pentaenylthio)-cyclobutanecarboxylate.

The present invention also relates to a lipid compound according of formula (I) for use as a medicament.

In a further aspect, the present invention provides a food supplement, a food additive, or a neutraceutical preparation comprising a lipid compound of formula (I).

Such a food supplement may be produced for administration through any route of administration. For example, the food supplement may be administered as a liquid nutritional or as a beverage.

The food supplement may be in the form of a capsule, e.g. a gelatine capsule, and the capsule may be flavoured.

In still a further aspect, the present invention provides a pharmaceutical composition comprising a compound of formula (I), preferably together with one or more pharmaceutically acceptable carriers or excipients.

The novel lipid compounds and compositions of the invention may be formulated in conventional oral administration forms, e.g. tablets, coated tablets, capsules, powders, granulates, solutions, dispersions, suspensions, syrups, emulsions, sprays, etc using conventional excipients, e.g. solvents, diluents, binders, sweeteners, aromas, pH modifiers, viscosity modifiers, antioxidants, corn starch, lactose, glucose, microcrystalline cellulose, magnesium stearate, polyvinylpyrrolidone, citric acid, tartaric acid, water, ethanol, glycerol, sorbitol, polyethylene glycol, propylene glycol, cetylstearyl alcohol, carboxymethylcellulose or fatty substances such as hard fat or suitable mixtures thereof etc. Conventional formulation techniques, well known in the art, may be used.

The compositions may likewise be administered by conventional administration routes, i.e. orally. The use of orally administrable compositions, e.g. tablets, coated tablets, capsules, syrups, etc is especially preferred.

A suitable daily dosage of the compound according to formula (I) is 1 mg to 10 g of said compound; 50 mg to 1 g of said compound, or 50 mg to 200 mg of said compound.

The pharmaceutical composition according to the invention may be used as a medicament.

The present invention also relates to lipid composition comprising a lipid compound according to formula (I). Suitably, at least 60% by weight, or at least 80% by weight of the lipid composition is comprised of said compound.

The lipid composition may further comprise a pharmaceutically acceptable antioxidant, e.g. tocopherol.

Further, the present invention relates to a lipid composition for use as a medicament.

Additionally, the present invention relates to the use of a lipid compound according to formula (I) for use in:
- activation or modulation of at least one of the human peroxisome proliferator-activated receptor (PPAR) isoforms α, γ or δ, wherein said compound e.g. is a pan-agonist or modulator
- the prevention and/or treatment of a dyslipidemic condition, e.g. hypertriglyceridemia (HTG)
- the prevention and/or treatment of elevated triglyceride levels, LDL cholesterol levels, and/or VLDL cholesterol levels
- the treatment and/or the prevention of obesity or an overweight condition
- the reduction of body weight and/or for preventing body weight gain
- the treatment and/or the prevention of a fatty liver disease, e.g. non-alcoholic fatty liver disease (NAFLD).
- the treatment and/or the prevention of atherosclerosis
- the prevention of myocardial infarction
- the treatment and/or the prevention of peripheral insulin resistance and/or a diabetic condition
- the treatment and/or prevention of type 2 diabetes
- the reduction of plasma insulin, blood glucose and/or serum triglycerides
- the treatment and/or the prevention of an inflammatory disease or condition The invention also relates to lipid compounds according to formula (I) for the treatment of the above mentioned conditions, and to methods for the treatment and/or prevention of the conditions listed above, comprising administering to a mammal in need thereof a pharmaceutically active amount of a compound according to formula (I).

In addition, the present invention encompasses methods for manufacturing lipid compounds according to formula (I). The raw material may e.g. originate from a vegetable, a microbial and/or an animal source, such as a marine fish oil. Preferably a marine oil or a krill oil is used.

DETAILED DESCRIPTION OF THE INVENTION

The present inventors have found that compounds of formula (I) as presented above, have remarkably good pharmaceutical activity.

As used herein, the term "lipid compound" relates to fatty acid analogues derived from e.g. saturated fatty acids, monounsaturated fatty acids, polyunsaturated fatty acids and lipids comprising 1-6 triple bonds.

A "pharmaceutically active amount" relates to an amount that will lead to the desired pharmacological and/or therapeutic effects, i.e. an amount of the combination product which is effective to achieve its intended purpose. While individual patient needs may vary, determination of optimal ranges for effective amounts of the combination product is within the skill of the art. Generally, the dosage regimen for treating a condition with the combination product of this invention is selected in accordance with a variety of factors, including the type, age, weight, sex, diet and medical condition of the patient.

By "a pharmaceutical composition" is meant a lipid compound according to the invention in any form suitable to be used for a medical purpose.

"Treatment" includes any therapeutic application that can benefit a human or non-human mammal. Both human and veterinary treatments are within the scope of the present invention. Treatment may be in respect of an existing condition or it may be prophylactic.

Nomenclature and Terminology

Fatty acids are straight chain hydrocarbons possessing a carboxyl (COOH) group at one end (α) and (usually) a methyl group at the other (ω) end. In chemistry, the numbering of the carbon atoms starts from the α end.

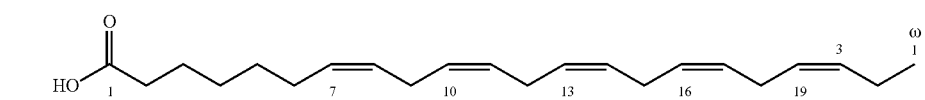

The α carbon refers to the first carbon after the carbon that attaches to the functional group, and the second carbon is the β carbon.

As used herein, the expression "methylene interrupted double bonds" relates to the case when a methylene group is located between to separate double bonds in a carbon chain of a lipid compound.

DETAILED DESCRIPTION OF THE INVENTION

The inventors have surprisingly found that the following lipid compound shown in categories A-E, are particularly preferable.

Category A
  derived from saturated fatty acids
  $R_1$ is a $C_{10}$-$C_{22}$ alkyl
  X represents a carboxylic acid or a derivative thereof, a carboxylic ester or a carboxamide Example i $R_1=C_{14}$, Y=S

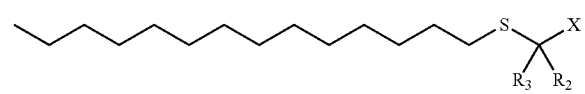

Category B
  derived from monounsaturated fatty acids
  $R_1$ is a $C_{10}$-$C_{22}$ alkenyl having 1 double bond
  X represents a carboxylic acid or a derivative thereof, a carboxylic ester or a carboxamide Example ii $R_1=C_{18}$, Y=S

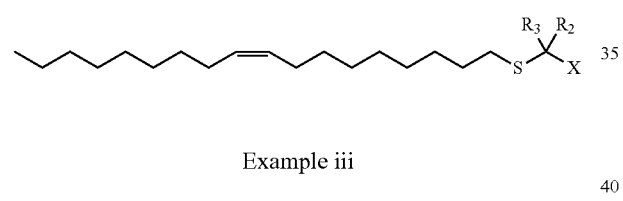

Example iii $R_1=C_{14}$, Y=S

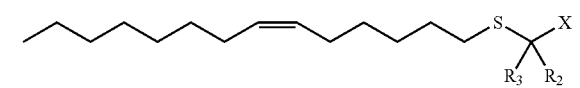

Category C
  derived from polyunsaturated fatty acids
  $R_1$ is a $C_{10}$-$C_{22}$ alkenyl having 2-6 double bonds
  X represents a carboxylic acid or a derivative thereof, a carboxylic ester or a carboxamide Example iv $R_1=C_{20}$ with 5 methylene interrupted double bonds in Z-configuration, Y=S

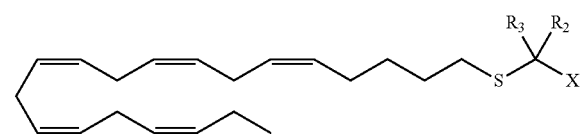

Example v $R_1=C_{22}$ with 6 methylene interrupted double bonds in Z-configuration, Y=S

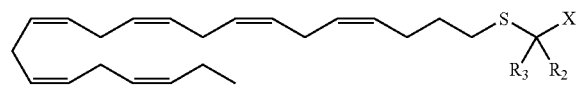

Example vi $R_1=C_{18}$ with 3 methylene interrupted double bonds in Z-configuration, Y=S

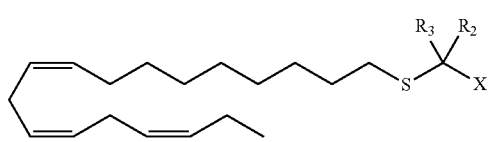

Example vii $R_1=C_{15}$ with 4 methylene interrupted double bonds in Z-configuration, Y=S

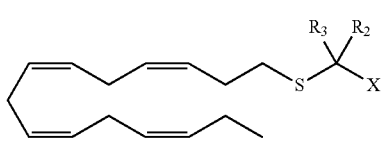

Example viii $R_1=C_{15}$ with 3 methylene interrupted double bonds in Z-configuration and 1 double bond in E-configuration, Y=S

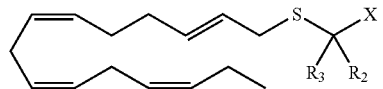

Example ix $R_1=C_{18}$ with 5 methylene interrupted double bonds in Z-configuration, Y=S

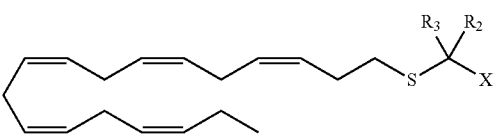

Example x $R_1=C_{18}$ with 4 methylene interrupted double bonds in Z-configuration and 1 double bond in E-configuration, Y=S

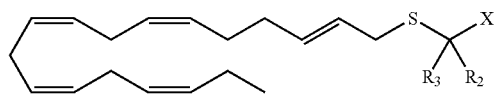

Category D
derived from lipids containing 1-6 triple bonds
$R_1$ is a $C_{10}$-$C_{22}$ alkynyl
X represents a carboxylic acid or a derivative thereof, a carboxylic ester or a carboxamide

Example xi $R_1=C_{14}$ with 1 triple bond, Y=S

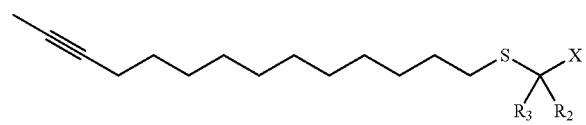

Category E
$R_1$ is selected from a $C_{10}$-$C_{22}$ alkyl, a $C_{10}$-$C_{22}$ alkenyl having 1-6 double bonds, and a $C_{10}$-$C_{22}$ alkynyl having 1-6 triple bonds
X represents a carboxylic acid or a derivative thereof, a carboxylic ester or a carboxamide
Y is sulfoxide or sulfone

Example xii $R_1=C_{15}$ with 4 methylene interrupted double bonds in Z-configuration, Y=SO

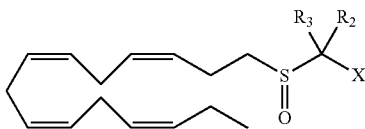

Example xiii $R_1=C_{15}$ with 4 methylene interrupted double bonds in Z-configuration, $Y=SO_2$

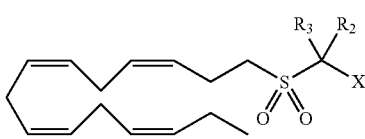

Specific examples of preferred lipid compounds according to the invention are:

Category A—Saturated Fatty Acids:

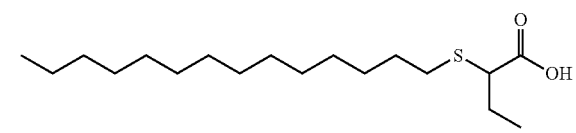 [SMILES: CCCCCCCCCCCCCCSC(CC)C(=O)O]

2-(tetradecylthio)butanoic acid (1)

$R_1=C_{14}H_{29}$, $R_2$=ethyl, $R_3$=a hydrogen atom, Y=S and X=COOH

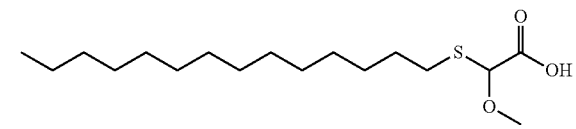 [SMILES: CCCCCCCCCCCCCCSC(OC)C(=O)O]

2-methoxy-2-(tetradecylthio)acetic acid (2)

$R_1=C_{14}H_{29}$, $R_2$=methoxy, $R_3$=a hydrogen atom, Y=S and X=COOH

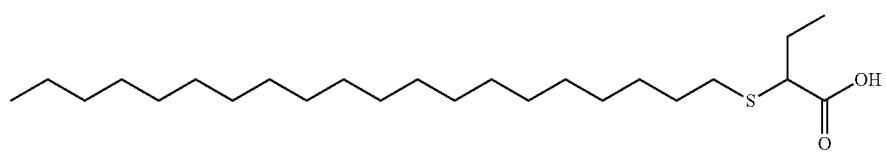 [SMILES: CCCCCCCCCCCCCCCCCCCCSC(CC)C(=O)O]

2-(icosylthio)butanoic acid (3)

$R_1=C_{20}H_{41}$, $R_2$=ethyl, $R_3$=a hydrogen atom, Y=S and X=COOH

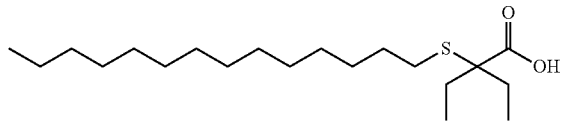 [SMILES: CCCCCCCCCCCCCCSC(CC)(CC)C(=O)O]

2-ethyl-2-(tetradecylthio)butanoic acid (4)

$R_1=C_{14}H_{29}$, $R_2=R_3$=ethyl, Y=S and X=COOH
Category B—Monounsaturated Fatty Acids:

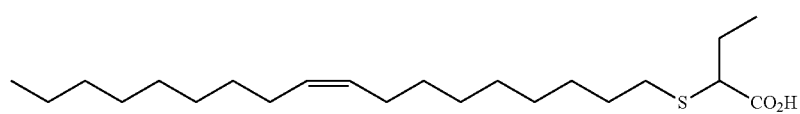 [SMILES: CCCCCCCC/C=C\CCCCCCCCSC(CC)C(=O)O]

2-ethyl-3-thia-12Z-heneicosaenoic acid (5)

$R_1=C_{18}H_{35}$, $R_2$=ethyl, $R_3$=a hydrogen atom, Y=S and X=COOH

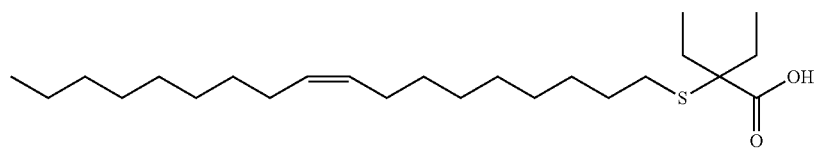 [SMILES: CCCCCCCC/C=C\CCCCCCCCSC(CC)(CC)C(=O)O]

(Z)-2-ethyl-2-(octadec-9-enylthio)butanoic acid (6)

$R_1=C_{18}H_{35}$, $R_2=R_3$=ethyl, Y=S and X=COOH
Category C—Polyunsaturated Fatty Acid Derivatives:

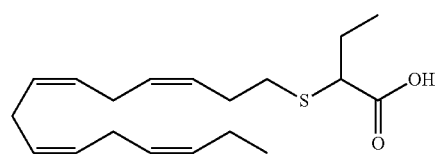 [SMILES: CC/C=C\C/C=C\C/C=C\C/C=C\CCSC(CC)C(=O)O]

2-((3Z,6Z,9Z,12Z)-pentadeca-3,6,9,12-tetraenylthio)butanoic acid (7)

$R_1=C_{15}H_{23}$, $R_2$=ethyl, $R_3$=a hydrogen atom, Y=S and X=COOH

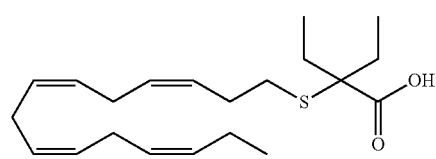 [SMILES: CC/C=C\C/C=C\C/C=C\C/C=C\CCSC(CC)(CC)C(=O)O]

2-ethyl-2-((3Z,6Z,9Z,12Z)-pentadeca-3,6,9,12-tetraenylthio)butanoic acid (8)

$R_1=C_{15}H_{23}$, $R_2=R_3$=ethyl, Y=S and X=COOH

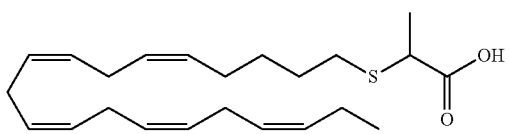 [SMILES: CC/C=C\C/C=C\C/C=C\C/C=C\C/C=C\CCCCSC(C)C(=O)O]

2-((5Z,8Z,11Z,14Z,17Z)-icosa-5,8,11,14,17-pentaenylthio)propanoic acid (9)

$R_1=C_{20}H_{31}$, $R_2$=methyl, $R_3$=a hydrogen atom, Y=S and X=COOH

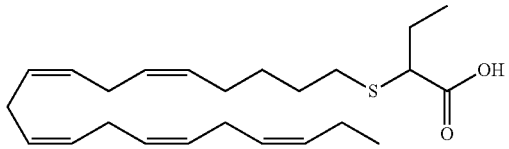 [SMILES: CC/C=C\C/C=C\C/C=C\C/C=C\C/C=C\CCCCSC(CC)C(=O)O]

2-((5Z,8Z,11Z,14Z,17Z)-icosa-5,8,11,14,17-pentaenylthio)butanoic acid (10)

$R_1=C_{20}H_{31}$, $R_2$=ethyl, $R_3$=a hydrogen atom, Y=S and X=COOH

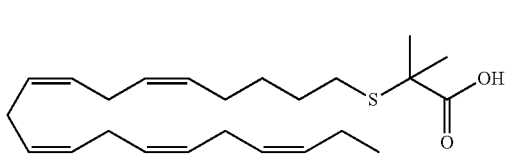

17

2-((5Z,8Z,11Z,14Z,17Z)-icosa-5,8,11,14,17-pentaenylthio)-2-methylpropanoic acid (11)

$R_1=C_{20}H_{31}$, $R_2$=methyl, $R_3$=methyl, Y=S and X=COOH

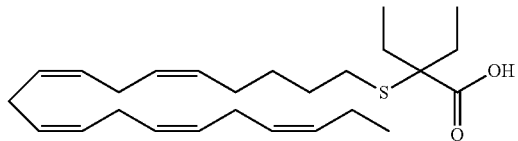 [SMILES: CC/C=C\C/C=C\C/C=C\C/C=C\C/C=C\CCCCSC(CC)(CC)C(=O)O]

2-ethyl-2-((5Z,8Z,11Z,14Z,17Z)-icosa-5,8,11,14,17-pentaenylthio)butanoic acid (12)

$R_1=C_{20}H_{31}$, $R_2=R_3$=ethyl, Y=S and X=COOH

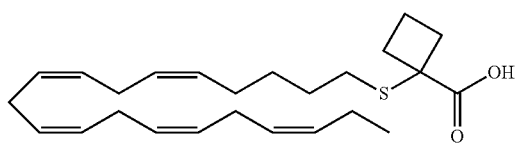 [SMILES: CC/C=C\C/C=C\C/C=C\C/C=C\C/C=C\CCCCSC1(C(=O)O)CCC1]

1-((5Z,8Z,11Z,14Z,17Z)-icosa-5,8,11,14,17-pentaenylthio)cyclobutanecarboxylic acid (13)

$R_1=C_{20}H_{31}$, $R_2$ and $R_3$ combines to form cyclobutane ring, Y=S and X=COOH

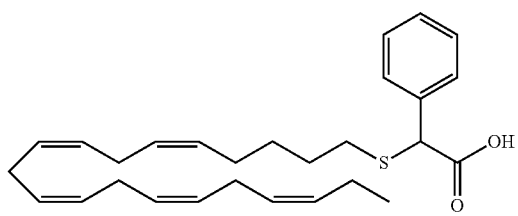 [SMILES: CC/C=C\C/C=C\C/C=C\C/C=C\C/C=C\CCCCSC(C(=O)O)c1ccccc1]

2-((5Z,8Z,11Z,14Z,17Z)-icosa-5,8,11,14,17-pentaenylthio)-2-phenylacetic acid (14)

$R_1=C_{20}H_{31}$, $R_2$=phenyl, $R_3$=a hydrogen atom, Y=S and X=COOH

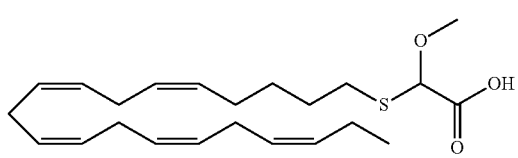 [SMILES: CC/C=C\C/C=C\C/C=C\C/C=C\C/C=C\CCCCSC(OC)C(=O)O]

18

2-((5Z,8Z,11Z,14Z,17Z)-icosa-5,8,11,14,17-pentaenylthio)-2-methoxyacetic acid (15)

$R_1=C_{20}H_{31}$, $R_2$=methoxy, $R_3$=a hydrogen atom, Y=S and X=COOH

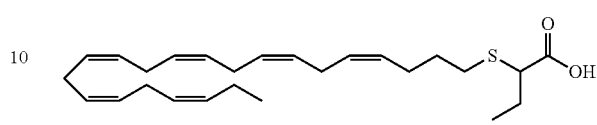

2-((4Z,7Z,10Z,13Z,16Z,19Z)-docosa-4,7,10,13,16,19-hexaenylthio)butanoic acid (16)

$R_1=C_{22}H_{33}$, $R_2$=ethyl, $R_3$=a hydrogen atom, Y=S and X=COOH

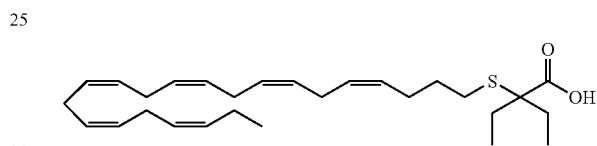

2-((4Z,7Z,10Z,13Z,16Z,19Z)-docosa-4,7,10,13,16,19-hexaenylthio)-2-ethylbutanoic acid (17)

$R_1=C_{22}H_{33}$, $R_2=R_3$=ethyl, Y=S and X=COOH

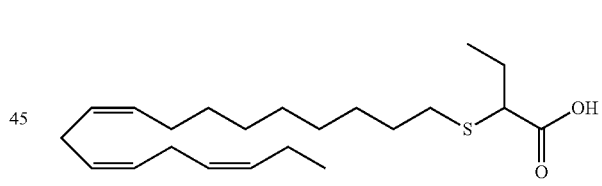

2-((9Z,12Z,15Z)-octadeca-9,12,15-trienylthio)butanoic acid (18)

$R_1=C_{18}H_{31}$, $R_2$=ethyl, $R_3$=a hydrogen atom, Y=S and X=COOH

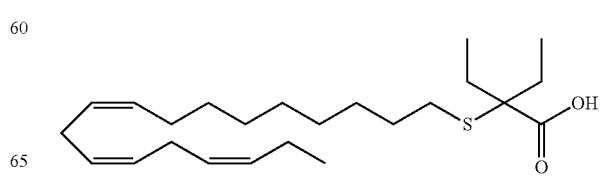

19

2-ethyl-2-((9Z,12Z,15Z)-octadeca-9,12,15-trienylthio)butanoic acid (19)

$R_1=C_{18}H_{31}$, $R_2=R_3=$ethyl, Y=S and X=COOH

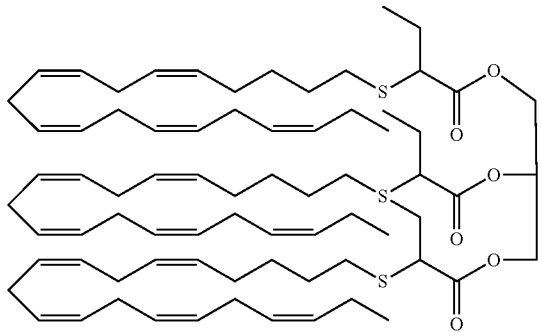

propane-1,2,3-triyl tris(2-((5Z,8Z,11Z,14Z,17Z)-icosa-5,8,11,14,17-pentaenylthio)butanoate) (20)

$R_1=C_{20}H_{31}$, $R_2=$ethyl, $R_3=$a hydrogen atom, Y=S and X=a carboxylic acid in the form of a triglyceride Category D—Triple Bond Containing Fatty Acids:

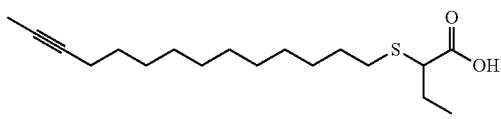 [SMILES: CC#CCCCCCCCCCCCSC(CC)C(=O)O]

2-(tetradec-12-ynylthio)butanoic acid (21)

$R_1=C_{14}H_{25}$, $R_2=$ethyl, $R_3=$a hydrogen atom, Y=S and X=COOH

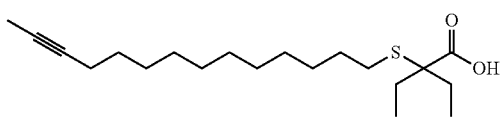 [SMILES: CC#CCCCCCCCCCCCSC(CC)(CC)C(=O)O]

2-ethyl-2-(tetradec-12-ynylthio)butanoic acid (22)

$R_1=C_{14}H_{25}$, $R_2=R_3=$ethyl, Y=S and X=COOH

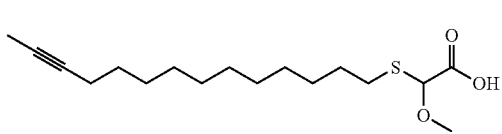 [SMILES: CC#CCCCCCCCCCCCSC(OC)C(=O)O]

20

2-methoxy-2-(tetradec-12-ynylthio)acetic acid (23)

$R_1=C_{14}H_{25}$, $R_2=$methoxy, $R_3=$a hydrogen atom, Y=S and X=COOH

Category E—Sulfones and Sulfoxides:

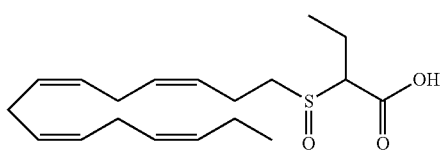 [SMILES: CC/C=C\C/C=C\C/C=C\C/C=C\CCS(=O)C(CC)C(=O)O]

2-((3Z,6Z,9Z,12Z)-pentadeca-3,6,9,12-tetraenylsulfinyl)butanoic acid (24)

$R_1=C_{15}H_{23}$, $R_2=$ethyl, $R_3=$a hydrogen atom, Y=SO and X=COOH

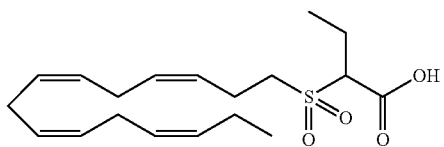

2-((3Z,6Z,9Z,12Z)-pentadeca-3,6,9,12-tetraenylsulfonyl)butanoic acid (25)

$R_1=C_{15}H_{23}$, $R_2=$ethyl, $R_3=$a hydrogen atom, Y=$SO_2$ and X=COOH

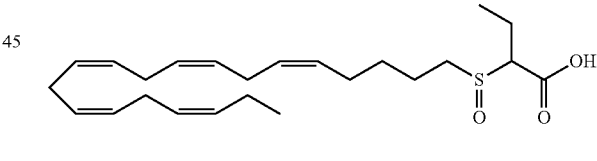

2-((5Z,8Z,11Z,14Z,17Z)-icosa-5,8,11,14,17-pentaenylsulfinyl)butanoic acid (26)

$R_1=C_{20}H_{31}$, $R_2=$ethyl, $R_3=$a hydrogen atom, Y=SO and X=COOH

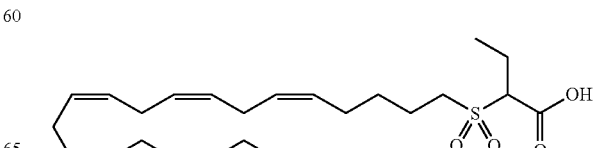

2-((5Z,8Z,11Z,14Z,17Z)-icosa-5,8,11,14,17-pentae-
nylsulfonyl)butanoic acid (27)

$R_1=C_{20}H_{31}$, $R_2$=ethyl, $R_3$=a hydrogen atom, $Y=SO_2$ and $X=COOH$

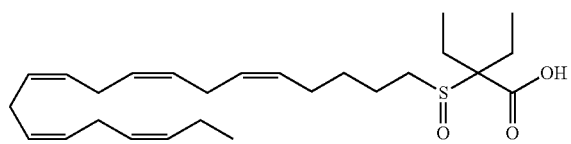 [SMILES: CC/C=C\C/C=C\C/C=C\C/C=C\C/C=C\CCCCS(=O)C(CC)(CC)C(=O)O]

2-ethyl-2-((5Z,8Z,11Z,14Z,17Z)-icosa-5,8,11,14,17-pentaenylsulfinyl)butanoic acid (28)

$R_1=C_{20}H_{31}$, $R_2=R_3$=ethyl, $Y=SO$ and $X=COOH$

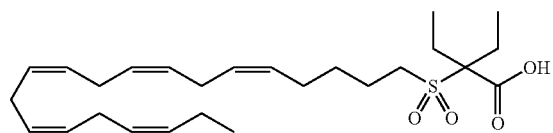 [SMILES: CC/C=C\C/C=C\C/C=C\C/C=C\C/C=C\CCCCS(=O)(=O)C(CC)(CC)C(=O)O]

2-ethyl-2-((5Z,8Z,11Z,14Z,17Z)-icosa-5,8,11,14,17-pentaenylsulfonyl)butanoic acid (29)

$R_1=C_{20}H_{31}$, $R_2=R_3$=ethyl, $Y=SO_2$ and $X=COOH$

The compounds of categories A-E above, were $R_2$ and $R_3$ are different, are capable of existing in stereoisomeric forms, i.e. all optical isomers of the compounds and mixtures thereof are encompassed. Hence, the said compounds may be present as diastereomers, racemates and enantiomers.

General Synthetic Methods for the Compounds Described Herein

The compounds of general formula (I) can be prepared by the following general procedures:

Method I

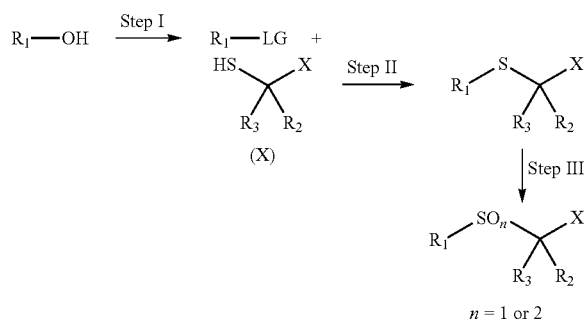

Method II

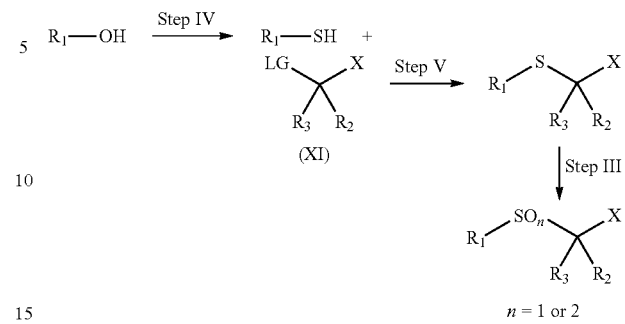

The alcohols described in method I and II may be prepared directly from the carboxylic esters of, for example, naturally occurring fatty acids; e.g. alpha-linolenic acid, conjugated linoleic acid, eicosapentaenoic acid (EPA), etc. by reduction with a reducing agent like lithium aluminiumhydride or diisobutylaluminiumhydride at −10 to 0° C. The alcohols can also be prepared by degradation of the polyunsaturated fatty acids EPA and DHA, as described by Holmeide et al. (*J. Chem. Soc., Perkin Trans.* 1, 2000, 2271). In this case one can start with purified EPA or DHA, but it is also possible to start with fish oil containing EPA and DHA in mixture.

Compounds of formula (X) and (XI) are commercially available, or they are known in the literature, or they are prepared by standard processes known in the art. The leaving group (LG) present in compounds of formula (XI) may, for example, be mesylate, tosylate or a suitable halogen, such as bromine.

Using method I, the resulting alcohols can be converted, using functional group interconversion, by methods familiar to persons skilled in the art (step I), to compounds where the terminal hydroxy group have been transformed into a suitable leaving group (LG). Suitable leaving groups include bromine, mesylate and tosylate. These compounds can be reacted further (step II) in a substitution reaction with the appropriately substituted thiol acetic acid derivatives (X), in the presence of base.

Using method II, the alcohols can be converted to the corresponding thiols (step IV) by methods familiar to persons skilled in the art. The thiols can then be reacted further (step V) in a substitution reaction with compounds of formula (XI), in the presence of base in an appropriate solvent system.

The corresponding sulfoxides and sulfones ($Y=SO$ or $SO_2$) can be prepared by oxidation of the thioethers ($Y=S$) with a suitable oxidising agent (step III). Examples of oxidising agents are m-chloro-perbenzoic acid (MCPBA), hydrogen peroxide ($H_2O_2$) and oxone (potassium peroxymonosulfate). By using 1 equivalent or less of the oxidising agent, the main product will be the sulfoxide. By using an excess oxidising agent, the main product will be the sulfone.

If the acid derivatives used are carboxylic esters, hydrolysis can be performed to obtain the free fatty acids. An esterifying group such as a methyl of an ethyl group may be removed, for example, by alkaline hydrolysis using a base such as an alkali metal hydroxide, for example LiOH, NaOH or KOH or by using an organic base, for example $Et_3N$ together with an inorganic salt, for example LiCl in an appropriate solvent system. A tert-butyl group may be removed, for example, by treatment with an acid, for example an organic acid such as trifluoroacetic acid or formic acid in an appropriate solvent system. An arylmethyl group such as a benzyl group may be removed, for example, by hydrogenation over a catalyst such as palladium-on-carbon in an appropriate solvent system.

The preparation of compounds of formula I, according to method I or II, may result in mixtures of stereoisomers. If required, these isomers may be separated by means of chiral resolving agents and/or by chiral column chromatography through methods known to the person skilled in the art.

Method III

The compounds of formula (I) wherein X is a carboxylic acid and in the form of a phospholipid can be prepared through the following processes.

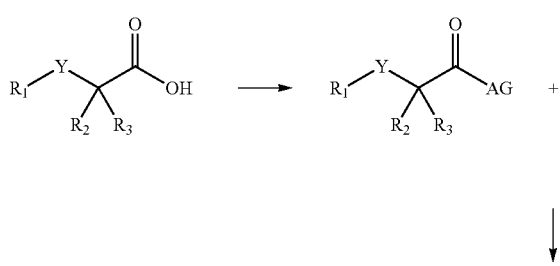

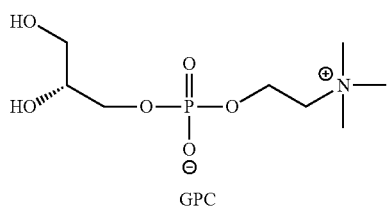

Acylation of sn-glycero-3-phosphocholine (GPC) with an activated fatty acid, such as fatty acid imidazolides, is a standard procedure in phosphatidylcholine synthesis. It is usually carried out in the presence of DMSO anion with DMSO as solvent (Hermetter; *Chemistry and Physics of lipids*, 1981, 28, 111). Sn-Glycero-3-phosphocholine, as cadmium (II) adduct can also be reacted with the imidazolide activated fatty acid in the presence of DBU (1,8-diazabicyclo[5.4.0]undec-7-ene) to prepare the phosphatidylcholine of the respective fatty acid (International application number PCT/GB2003/002582). Enzymatic transphosphatidylation can effect the transformation of phosphatidylcholine to phosphatidylethanolamine (Wang et al, *J. Am. Chem. Soc.*, 1993, 115, 10487).

Phospholipids may also be prepared by enzymatic esterification and transesterification of phospholipids or enzymatic transphosphatidylation of phospholipids. (Hosokawa, *J. Am. Oil Chem. Soc.* 1995, 1287, Lilja-Hallberg, *Biocatalysis*, 1994, 195).

Method IV

The compounds of formula (I) wherein X is a carboxylic acid and in the form of a triglyceride can be prepared through the following process. Excess of the fatty acid can be coupled to glycerol using dimethylaminopyridine (DMAP) and 2-(1H-benzotriazol-1-yl)-N,N,N',N'-tetramethyluroniumhexafluorophosphate (HBTU).

Method V

The compounds of formula (I) wherein X is a carboxylic acid in the form of a diglyceride can be prepared by reaction of the fatty acid (2 equivalents) with glycerol (1 equivalent) in the presence of 1,3-dicyclohexylcarbondiimide (DCC) and 4-dimethylaminopyridine (DMAP).

Method VI

The compounds of formula (I) wherein X is a carboxylic acid and in the form of a monoglyceride can be prepared through the following processes.

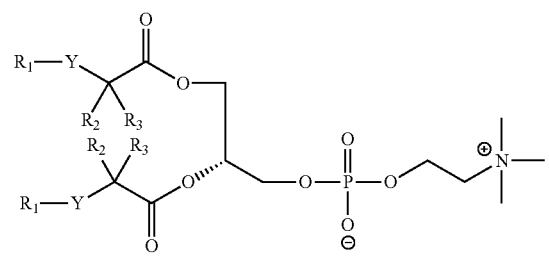

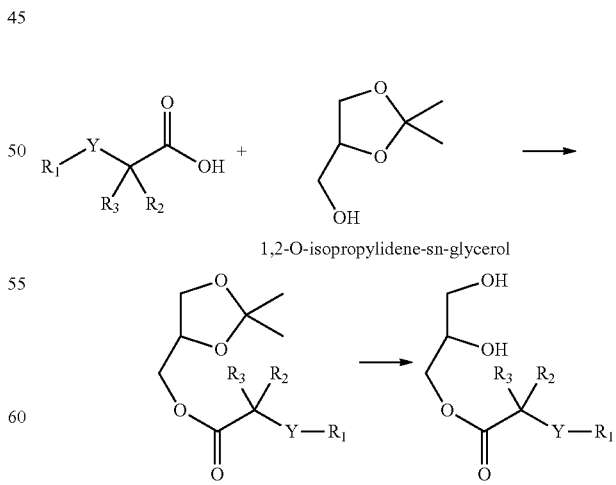

Acylation of 1,2-O-isopropylidene-sn-glycerol with a fatty acid using DCC and DMAP in chloroform gives a monodienoylglycerol. Deprotection of the isopropylidene group can be done by treating the protected glycerol with an acidic (HCl, acetic acid etc.) (O'Brian, *J. Org. Chem.*, 1996, 5914).

There are several synthetic methods for the preparation of monoglycerides with the fatty acid in 2-position. One method utilizes esterification of the fatty acid with glycidol in the presence of 1-(3-dimethylaminopropyl)-3-ethylcarbodiimi-dehydrochloride (EDC) and 4-dimethylaminopyridine (DMAP) to produce a glycidyl derivative. Treatment of the glycidyl derivative with trifluoroacetic anhydride (TFAA) prior to trans-esterification the monoglyceride is obtained (Parkkari et al, *Bioorg. Med. Chem. Lett.* 2006, 2437).

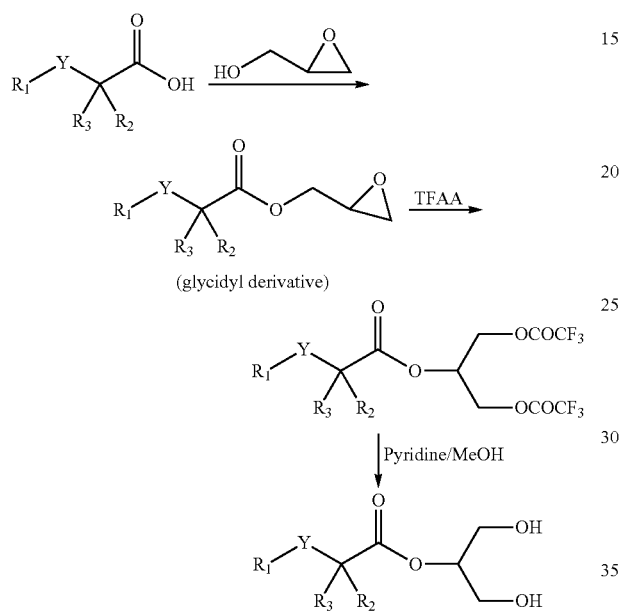

(glycidyl derivative)

Further methods for the preparation of mono-, di- and tri-glycerides of fatty acid derivatives are described in international patent application, PCT/FR02/02831.

It is also possible to use enzymatic processes (lipase reactions) for the transformation of a fatty acid to a mono-, di-, tri-glyceride. A 1,3-regiospecific lipase from the fungus *Mucor miehei* can be used to produce triglycerides or diglycerides from polyunsaturated fatty acids and glycerol. A different lipase, the non-regiospecific yeast lipase from *Candida antartica* is highly efficient in generating triglycerides from polyunsaturated fatty acids (Haraldsson, *Pharmazie*, 2000, 3).

Preparation, Characterisation and Biological Testing of Specific Fatty Acid Derivatives of Formula (I)

The invention will now be further described by the following non-limiting examples, in which standard techniques known to the skilled chemist and techniques analogous to those described in these examples may be used where appropriate. Unless otherwise stated:

evaporations were carried out by rotary evaporation in vacuo;

all reactions were carried out at room temperature, typically in the range between 18-25° C. with solvents of HPLC grade under anhydrous conditions;

column chromatography were performed by the flash procedure on silica gel 40-63 μm (Merck) or by an Armen Spoflash using the pre-packed silica gel columns "MiniVarioFlash", "SuperVarioFlash", "SuperVarioPrep" or "EasyVarioPrep" (Merck);

yields are given for illustration only and are not necessarily the maximum attainable;

the nuclear magnetic resonance (NMR) shift values were recorded on a Bruker Avance DPX 200 or 300 instrument, and the peak multiplicities are shown as follows: s, singlet; d, doublet; dd, double doublet; t, triplet; q, quartet; p, pentet; m, multiplet; br, broad;

the mass spectra were recorded with a LC/MS spectrometer. Separation was performed using a Agilent 1100 series module on a Eclipse XDB-C18 2.1×150 mm column with gradient elution. As eluent were used a gradient of 5-95% acetonitrile in buffers containing 0.01% trifluoroacetic acid or 0.005% sodium formate. The mass spectra were recorded with a G 1956 A mass spectrometer (electrospray, 3000 V) switching positive and negative ionization mode.

Preparation of Intermediates

Example 1

Preparation of S-(3Z,6Z,9Z,12Z)-pentadeca-3,6,9,12-tetraenyl ethanethioate

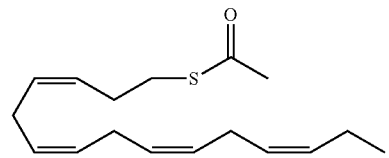 [SMILES: CC/C=C\C/C=C\C/C=C\C/C=C\CCSC(C)=O]

Triphenylphosphine (PPh₃) (41.7 g, 159 mmol) was dissolved in dry tetrahydrofurane (THF) (250 mL) at 0° C. under inert atmosphere and added diisopropyl azodicarboxylate (DIAD) (30.8 mL, 159 mmol). The mixture was stirred at 0° C. for 40 minutes and then dropwise added a solution of (all-Z)-3,6,9,12-pentadecatetraenol (17.5 g, 79.4 mmol) and thioacetic acid (11.4 mL, 159 mmol) in dry THF (150 mL). The resulting turbid mixture was stirred at 0° C. for 40 minutes, then at ambient temperature for two hours. Heptane was added (300 mL), the mixture was stirred for ten minutes and the precipitated white solid was removed by filtration. This procedure was repeated twice and finally the residue after concentration was stirred in heptane (100 mL) for 16 hours. Filtration and purification of the residue by flash chromatography (1% EtOAc in heptane) provided 13.7 g (62% yield) of the title compound as an oil.

¹H-NMR (200 MHz, CDCl₃): δ 0.96 (t, 3H), 2.05 (m, 2H), 2.31 (s+m, 5H), 2.76-2.92 (m, 8H), 5.32-5.45 (m, 8H).

Example 2

Preparation of (3Z,6Z,9Z,12Z)-pentadeca-3,6,9,12-tetraene-1-thiol

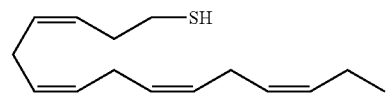

LiAlH₄ (2.05 g, 54.1 mmol) was suspended in dry diethyl ether (100 mL) at 0° C. under inert atmosphere. To this suspension was added dropwise a solution of S-(3Z,6Z,9Z,12Z)-pentadeca-3,6,9,12-tetraenyl ethanethioate (13.7 g, 49.2 mmol) in dry diethyl ether (50 mL) and the resulting grey mixture was stirred at 0° C. for ten minutes and then at ambient temperature for 30 minutes. The mixture was cooled to ~5° C., added 1M HCl until pH=2 and filtrated through a short pad of celite. The pad was washed with water and diethyl ether, the phases were separated and the aqueous phase was extracted twice with diethyl ether (100 mL each). The combined organic extracts were dried (Na$_2$SO$_4$), filtered and concentrated under reduced pressure to afford 7.8 g (67% yield) of the title compound as oil.

$^1$H-NMR (200 MHz, CDCl$_3$): δ 0.96 (t, 3H), 2.06 (m, 2H), 2.39 (m, 2H), 2.51 (m, 2H), 2.81 (m, 6H), 5.28-5.54 (m, 8H); MS (ESI): 235 [M−H]$^−$.

Example 3

Preparation of S-(5Z,8Z,11Z,14Z,17Z)-icosa-5,8,11,14,17-pentaenyl ethanethioate

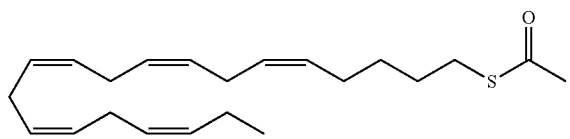 [SMILES: CC/C=C\C/C=C\C/C=C\C/C=C\C/C=C\CCCCSC(C)=O]

Triphenylphosphine (21.0 g, 80 mmol) was dissolved in dry THF (170 mL) at 0° C. under inert atmosphere and added DIAD (15.8 mL, 80 mmol) dropwise. After 40 minutes at 0° C. the white suspension was added dropwise to a solution of (5Z,8Z,11Z,14Z,17Z)-icosa-5,8,11,14,17-pentaen-1-ol (11.5 g, 40 mmol) and thioacetic acid (5.7 mL, 80 mmol) in dry THF (50 mL) during 15 minutes. The resulting turbid mixture was stirred at 0° C. for 30 minutes, followed by ambient temperature for 1.5 hour. Heptane was added (200 mL), the mixture was stirred for ten minutes and the precipitated white solid removed by filtration and rinsed with heptane (150 mL). The residue was concentrated to remove most of the THF and stirred at ambient for 18 hours. The mixture was filtered, concentrated and added heptane (200 mL). The resulting mixture was stirred for 2 hours, filtered and evaporated. The residue was purified by flash chromatography on silica gel, using EtOAc:Heptane (2:98), followed by EtOAc:Heptane (4:96) and finally EtOAc:Heptane (5:95). Concentration of the appropriate fractions provided 11.0 g (79% yield) of the title compound as oil.

$^1$H-NMR (300 MHz, CDCl$_3$): δ 0.95 (t, 3H, J=7.5 Hz), 1.40 (m, 2H), 1.58 (m, 2H), 2.06 (m, 4H), 2.29 (s, 3H), 2.77-2.87 (m, 10H), 5.25-5.42 (m, 10H); MS (Cl(CH$_4$)): 387 [M+C$_3$H$_5$]$^+$, 375 [M+C$_2$H$_5$]$^+$, 347 [M+H]$^+$, 333 [M−CH$_2$]$^+$, 305 [R−SH]$^+$.

Example 4

Preparation of (5Z,8Z,11Z,14Z,17Z)-icosa-5,8,11,14,17-pentaene-1-thiol

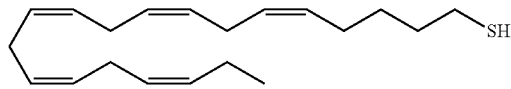 [SMILES: CC/C=C\C/C=C\C/C=C\C/C=C\C/C=C\CCCCS]

S-(5Z,8Z,11Z,14Z,17Z)-Icosa-5,8,11,14,17-pentaenyl ethanethioate (7.00 g, 20.2 mmol) was dissolved in MeOH (100 mL) by stirring 10 minutes until the droplets of oil dissolved, before anhydrous potassium carbonate, K$_2$CO$_3$ (2.79 g, 20.2 mmol) was added in one portion. The mixture was stirred for 1 hour and 20 minutes at ambient temperature and quenched by addition of 1 M HCl (50 mL) and water (150 mL). The white cloudy mixture was added Et$_2$O (250 mL) and the phases were separated. The water phase was extracted with Et$_2$O (2×250 mL). The combined organic phases were washed with brine (250 mL) and dried (MgSO$_4$). Filtration and evaporation gave the title compound as oil (5.99 g, 97% yield), which was used without further purification.

$^1$H-NMR (300 MHz, CDCl$_3$): δ 0.96 (t, 3H, J=7.5 Hz), 1.31 (t, 1H, J=7.8 Hz), 1.44 (m, 2H), 1.61 (m, 2H), 2.06 (m, 4H), 2.51 (m, 2H), 2.77-2.85 (m, 8H), 5.28-5.41 (m, 10H); MS (Cl(CH$_4$)): 345 [M+C$_3$H$_5$]$^+$, 333 [M+C$_2$H$_5$]$^+$, 305 [M+H]$^+$, 271 [M−SH]$^+$.

Example 5

Preparation of (5Z,8Z,11Z,14Z,17Z)-icosa-5,8,11,14,17-pentaenyl methanesulfonate

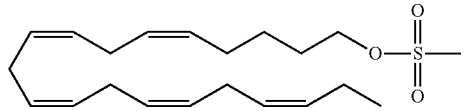 [SMILES: CC/C=C\C/C=C\C/C=C\C/C=C\C/C=C\CCCCOS(C)(=O)=O]

Et$_3$N (1.50 mL, 10.8 mmol) and methanesulfonyl chloride (402 μL, 5.20 mmol) was added to a solution of (5Z,8Z,11Z,14Z,17Z)-icosa-5,8,11,14,17-pentaen-1-ol (1.15 g, 4.0 mmol) in CH$_2$Cl$_2$ (40 mL) held at 0° C. under nitrogen. The mixture was stirred at 0° C. for one hour, and poured into ice-water (100 g) and the water phase extracted with Et$_2$O (50 mL). The combined organic extracts were added 0.5 M H$_2$SO$_4$ (35 mL), the organic phase washed with NaHCO$_3$ (sat. aq.) (25 mL), before dried (Mg$_2$SO$_4$, gram). Filtration and concentration in vacuo afforded 1.24 gram of crude oil. Purification on Armen, SVP D26 column packed with 30 gram of 15-40 μm Merck silica, flow 20 mL/min, UV 210 nm and collecting 15 mL fraction, was performed using gradient elution: (starting heptane:EtOAc (100:0) and increasing during 10 min. to 10% EtOAc, then increasing 5 min. to 20% EtOAc (hold 10 min.), then increasing in 5 min. to 40% EtOAc (hold 0 min.). Fractions 6-14 afforded 1.16 g (79% yield) of the title compound as oil.

$^1$H-NMR (300 MHz, CDCl$_3$): δ 0.97 (t, 3H), 1.50 (m, 2H), 1.75 (m, 2H), 2.03-2.15 (m, 4H), 2.76-2.86 (m, 8H), 2.99 (s, 3H), 4.22 (t, 2H), 5.27-5.40 (m, 10H); MS (electrospray): 389.2 [M+Na]$^+$.

Example 6

Preparation of (4S,5R)-3-((S)-2-((5Z,8Z,11Z,14Z, 17Z)-icosa-5,8,11,14,17-pentaenylthio)butanoyl)-4-methyl-5-phenyloxazolidin-2-one and (4S,5R)-3-((R)-2-((5Z,8Z,11Z,14Z,17Z)-icosa-5,8,11,14,17-pentaenylthio)butanoyl)-4-methyl-5-phenyloxazolidin-2-one

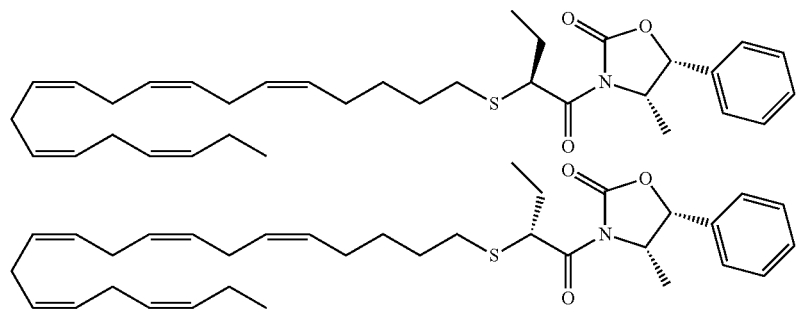

A mixture of 2-((5Z,8Z,11Z,14Z,17Z)-icosa-5,8,11,14,17-pentaenylthio)butanoic acid (3.0 g, 7.9 mmol) in dry dichloromethane (40 mL) held at 0° C. under nitrogen was added DMAP (1.0 g, 9.5 mmol) and 1,3-dicyclohexylcarbodiimide (DCC) (1.8 g, 8.7 mmol). The resulting mixture was stirred at 0° C. for 20 minutes, (4S,5R)-4-methyl-5-phenyl-2-oxazolidinone (1.7 g, 9.5 mmol) was added and the resulting turbid mixture was stirred at ambient temperature for 24 hours. The mixture was filtrated and concentrated under reduced pressure to give a crude product containing the desired product as a mixture of two diastereomers. The residue was purified by flash chromatography on Armen Spot-flash instrument on silica gel using 2% ethyl acetate in heptane as eluent. The two diastereomers were separated and the appropriate fractions were concentrated. (4S,5R)-3-((R)-2-((5Z,8Z,11Z,14Z,17Z)-Icosa-5,8,11,14,17-pentaenylthio) butanoyl)-4-methyl-5-phenyloxazolidin-2-one eluted first and was obtained in 0.95 g (47% yield) as an oil. 1.47 g (67% yield) of (4S,5R)-3-((S)-2-((5Z,8Z,11Z,14Z,17Z)-icosa-5,8,11,14,17-pentaenylthio)butanoyl)-4-methyl-5-phenyloxazolidin-2-one was obtained as an oil.

(4S,5R)-3-((R)-2-((5Z,8Z,11Z,14Z,17Z)-Icosa-5,8,11,14,17-pentaenylthio)butanoyl)-4-methyl-5-phenyloxazolidin-2-one (E1)

$^1$H-NMR (300 MHz, CDCl$_3$): δ 0.93-1.06 (m, 9H), 1.45-1.60 (m, 4H), 1.75-1.85 (m, 1H), 2.05-2.15 (m, 5H), 2.55-2.70 (m, 2H), 2.87 (m, 8H), 4.69 (t, 1H), 4.79 (p, 1H), 5.30-5.45 (m, 10H), 5.72 (d, 1H), 7.32 (m, 2H), 7.43 (m, 3H).

(4S,5R)-3-((S)-2-((5Z,8Z,11Z,14Z,17Z)-Icosa-5,8,11,14,17-pentaenylthio)butanoyl)-4-methyl-5-phenyloxazolidin-2-one $^1$H-NMR (300 MHz, CDCl$_3$): δ 0.93 (d, 3H), 0.99 (t, 3H), 1.05 (t, 3H), 1.40-1.56 (m, 4H), 1.50-1.75 (m, 1H), 2.00-2.15 (m, 5H), 2.47-2.65 (m, 2H), 2.83 (m, 8H), 4.62 (t, 1H), 4.85 (p, 1H), 5.25-5.45 (m, 10H), 5.70 (d, 1H), 7.32 (m, 2H), 7.43 (m, 3H).

Preparation of Target Molecules

Example 7

Preparation of ethyl 2-((3Z,6Z,9Z,12Z)-pentadeca-3,6,9,12-tetraenylthio)butanoate (30)

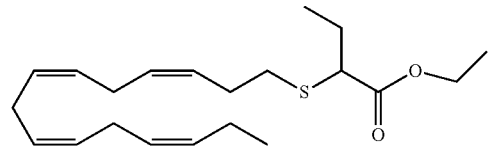 [SMILES: CC/C=C\C/C=C\C/C=C\C/C=C\CCSC(CC)C(=O)OCC]

A solution of 3Z,6Z,9Z,12Z)-pentadeca-3,6,9,12-tetraene-1-thiol (9.80 g, 41.5 mmol) in dry dimethylformamide (DMF) (70 mL) at 0° C. under inert atmosphere was added NaH (60% in mineral oil, 1.82 g, 45.6 mmol) and stirred at this temperature for ten minutes. Ethyl bromobutyrate (6.39 mL, 43.5 mmol) was added and the mixture was stirred at ambient temperature for 30 minutes. The mixture was partitioned between saturated NH$_4$Cl (150 mL) and heptane (150 mL). The aqueous layer was extracted twice with heptane (100 mL each) and the combined organic extract were washed with water (100 mL) and brine (100 mL). The organic layer was dried (Na$_2$SO$_4$), filtrated and concentrated. The residue was purification by flash chromatography on silica gel (heptane: EtOAc 99:1 then 95:5). Concentration of the appropriate fractions afforded 14.1 g (97% yield) of the title compound as oil.

$^1$H-NMR (200 MHz, CDCl$_3$): δ 0.92-1.01 (2×t, 6H), 1.27 (t, 3H), 1.60-1.80 (m, 1H), 1.80-1.95 (m, 1H), 2.00-2.15 (m, 2H) 2.25-2.45 (m, 2H), 2.60-2.75 (m, 2H), 2.80 (m, 6H), 3.15 (t, 1H), 4.17 (q, 2H), 5.31-5.43 (m, 8H); MS (ESI): 373 [M+Na]$^+$.

Example 8

Preparation of ethyl 2-((3Z,6Z,9Z,12Z)-pentadeca-3,6,9,12-tetraenylsulfonyl)butanoate (31)

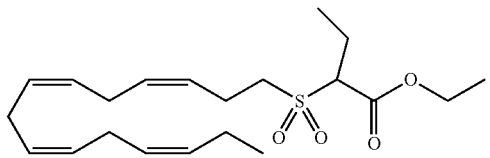 [SMILES: CC/C=C\C/C=C\C/C=C\C/C=C\CCS(=O)(=O)C(CC)C(=O)OCC]

Ethyl 2-((3Z,6Z,9Z,12Z)-pentadeca-3,6,9,12-tetraenylthio)butanoate (2.7 g, 7.7 mmol) was dissolved in dry CHCl₃ (40 mL) and the solution was cooled down to −20° C. under inert atmosphere. meta-Chloroperoxybenzoic acid (mCPBA) (~77%, 4.0 g, 18 mmol) dissolved in dry CHCl₃ (10 mL) was added dropwise and the resulting solution was stirred at −20° C. for 30 minutes, allowed to slowly reach ambient temperature and then stirred over night. The solvents were evaporated in vacuo, the residue was added heptane (30 mL) and the resulting white precipitate was removed by filtration. The filtrate was concentrated in vacuo and the residue was added heptane (10 mL). The resulting white precipitate was again removed by filtration. The filtrate was concentrated in vacuo and the residue was purified by flash chromatography on silica gel (heptane:EtOAc 4:1). Concentration of the appropriate fractions afforded 0.37 g (13% yield) of the title compound as an oil.

$^1$H NMR (300 MHz, CDCl₃): δ 0.96 (t, 3H), 1.03 (t, 3H), 1.31 (t, 3H), 2.02-2.15 (m, 4H), 2.62 (m, 2H), 2.82 (m, 6H), 3.05 (m, 1H), 3.20 (m, 1H), 3.70 (dd, J=10.3 Hz, J=4.7 Hz, 1H), 4.28 (q, 2H), 5.26-5.41 (m, 7H), 5.46-5.52 (m, 1H); MS (electrospray): 405.2 [M+Na]$^+$

Example 9

Preparation of 2-((3Z,6Z,9Z,12Z)-pentadeca-3,6,9,12-tetraenylthio)butanoic acid (7)

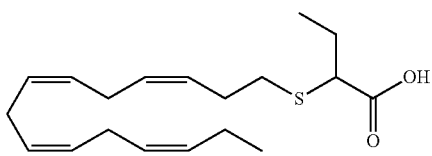 [SMILES: CC/C=C\C/C=C\C/C=C\C/C=C\CCSC(CC)C(=O)O]

Ethyl 2-((3Z,6Z,9Z,12Z)-pentadeca-3,6,9,12-tetraenylthio)butanoate (14.1 g, 40.2 mmol) was dissolved in ethanol (200 mL) and added a solution of LiOH×H₂O (13.5 g, 322 mmol) in water (50 mL). The resulting turbid solution was stirred at 70° C. under inert atmosphere for 90 minutes, cooled, added water (100 mL) and 3M HCl until pH=2. The mixture was extracted three times with heptane (100 mL each). The combined organic extracts were dried (Na₂SO₄), filtered and concentrated under reduced pressure to afford 11.8 g (91% yield) of the title compound as oil.

$^1$H-NMR (200 MHz, CDCl₃): δ 0.91-1.06 (2×t, J=7.2 Hz, J=7.5 Hz, 6H), 1.60-1.80 (m, 1H), 1.80-1.95 (m, 1H), 2.05 (p, J=7.2 Hz, 2H), 2.35 (m, 2H), 2.60-2.75 (m, 2H), 2.75-2.90 (m, 6H), 3.14 (t, J=7.1 Hz, 1H), 5.31-5.47 (m, 8H); MS (ESI): 321 [M−H]$^−$.

Example 10

Preparation of 2-((3Z,6Z,9Z,12Z)-pentadeca-3,6,9,12-tetraenylsulfinyl)butanoic acid (24)

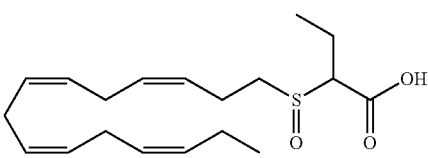 [SMILES: CC/C=C\C/C=C\C/C=C\C/C=C\CCS(=O)C(CC)C(=O)O]

2-((3Z,6Z,9Z,12Z)-Pentadeca-3,6,9,12-tetraenylthio)butanoic acid (0.20 g, 0.62 mmol) was dissolved in dry CHCl₃ (10 mL) and the solution was cooled down to −20° C. under inert atmosphere. mCPBA (~77%, 0.15 g, 0.68 mmol) dissolved in dry CHCl₃ (2 mL) was added dropwise and the resulting solution was stirred at −20° C. for 35 minutes. The solvents were evaporated in vacuo, the residue was added heptane (10 mL) and the resulting white precipitate was removed by filtration. The filtrate was concentrated in vacuo and the residue was added heptane (10 mL). The resulting white precipitate was again removed by filtration. The filtrate was concentrated in vacuo and the residue was purified by flash chromatography on silica gel (heptane:EtOAc+$^w$/1% HCOOH 4:1-1:1). Concentration of the appropriate fractions afforded 100 mg (48% yield) of the title compound as an oil.

$^1$H NMR (200 MHz, CDCl₃): δ 0.95 (t, 3H), 1.10 (2×q, 3H), 1.70-1.80 (m, 1H), 2.05 (m, 3.5H), 2.20-2-40 (m, 0.5H), 2.60 (m, 2H), 2.81 (m, 7H), 2.90-3.00 (m, 0.5H), 3.10-3.25 (m, 1H), 3.70 (dd, 0.5H), 5.25-5.55 (m, 8H); MS (electrospray): 337.1 [M−H]$^−$

Example 11

Preparation of 2-((3Z,6Z,9Z,12Z)-pentadeca-3,6,9,12-tetraenylsulfonyl)butanoic acid (25)

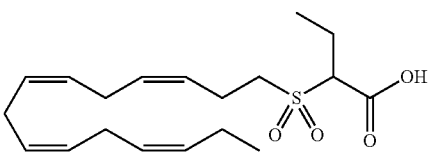 [SMILES: CC/C=C\C/C=C\C/C=C\C/C=C\CCS(=O)(=O)C(CC)C(=O)O]

Ethyl 2-((3Z,6Z,9Z,12Z)-pentadeca-3,6,9,12-tetraenylsulfonyl)butanoate (370 mg, 0.97 mmol) was dissolved in ethanol (10 mL) and added a solution of LiOH in H₂O (1 M, 3.9 mL, 3.9 mmol). The resulting mixture was stirred at 60° C. for three hours, cooled, added 0.1 M HCl until pH=2 and extracted twice with diethyl ether (15 mL each). The combined organic layer was washed with brine (15 mL), dried, filtrated, concentrated in vacuo and purified by flash chromatography on silica gel (heptane:EtOAc $^w$/5% HCOOH 4:1). Concentration of the appropriate fractions afforded 250 mg (73% yield) of the title compound as an oil.

$^1$H NMR (300 MHz, CDCl₃): δ 0.96 (t, 3H), 1.09 (t, 3H), 2.02-2.25 (m, 4H), 2.65 (m, 2H), 2.82 (m, 6H), 3.10 (m, 1H), 3.20 (m, 1H),

Example 12

Preparation of ethyl 2-((5Z,8Z,11Z,14Z,17Z)-icosa-5,8,11,14,17-pentaenylthio)propanoate (32)

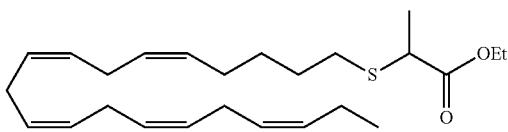 [SMILES: CC/C=C\C/C=C\C/C=C\C/C=C\C/C=C\CCCCSC(C)C(=O)OCC]

(5Z,8Z,11Z,14Z,17Z)-Icosa-5,8,11,14,17-pentaene-1-thiol (305 mg, 1.00 mmol) was added to a solution of NaH (60% in mineral oil, 44 mg, 1.10 mmol) in dry DMF (10 mL) held at 0° C. under inert atmosphere. After ten minutes ethyl bromopropionate (136 μL, 1.05 mmol) was added and the mixture was stirred for 1.5 hour at 0° C. The reaction mixture was added sat. aq. NH$_4$Cl (20 mL) and heptane (50 mL). The phases were separated and the water phase extracted with heptane (2×25 mL). The combined organics were washed with brine (25 mL), dried (MgSO$_4$), filtered and evaporated to give 376 mg of title compound as crude oil. Purification by flash chromatography on silica gel using gradient elution (starting pure heptane and increasing stepwise to heptane:EtOAc 95:5) afforded 318 mg (79% yield) of the title compound as oil.

$^1$H-NMR (300 MHz, CDCl$_3$): δ 0.95 (t, 3H), 1.25 (t, 3H), 1.41 (d, 3H), 1.44 (m, 2H), 1.58 (m, 2H), 2.06 (m, 4H), 2.60 (m, 2H), 2.71-2.85 (m, 8H), 3.36 (d, 1H), 4.17 (m, 2H), 5.25-5.40 (m, 10H); MS (Cl(CH$_4$)): 445 [M+C$_3$H$_5$]$^+$, 433 [M+C$_2$H$_5$]$^+$, 405 [M+H]$^+$, 359 [M−OEt]$^+$, 331 [M−CO$_2$Et]$^+$, 303 [R−S].$^+$.

Example 13

Preparation of ethyl 2-((5Z,8Z,11Z,14Z,17Z)-icosa-5,8,11,14,17-pentaenylthio)butanoate (33)

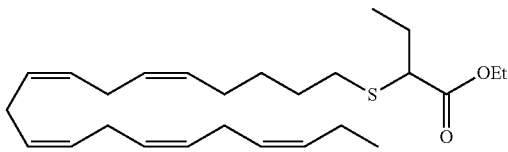 [SMILES: CC/C=C\C/C=C\C/C=C\C/C=C\C/C=C\CCCCSC(CC)C(=O)OCC]

To a solution of (5Z,8Z,11Z,14Z,17Z)-icosa-5,8,11,14,17-pentaene-1-thiol (305 mg, 1.00 mmol) in dry DMF (10 mL) at 0° C. under inert atmosphere was added NaH (60% in mineral oil, 44 mg, 1.1 mmol). After fifteen minutes ethyl bromobutyrate (154 μL, 1.05 mmol) was added. The mixture was stirred for 1 hour at 0° C. Sat. aq. NH$_4$Cl (20 mL), water (20 mL) and heptane (50 mL) were added. The phases were separated and the water phase was extracted with heptane (2×25 mL). The combined organics were washed with water (25 mL) and brine (25 mL), dried (MgSO$_4$), filtered and evaporated to give 379 mg of the title compound as a crude oil. Purification by flash chromatography on silica gel using gradient elution (starting pure heptane and increasing stepwise to heptane:EtOAc 95:5) afforded 345 mg (82% yield) of the title compound as oil.

$^1$H-NMR (300 MHz, CDCl$_3$): δ 0.93-1.00 (m, 6H), 1.25 (t, 3H), 1.44 (m, 2H), 1.59 (m, 2H), 1.68 (m, 1H), 1.87 (m, 1H), 2.07 (m, 4H), 2.57 (m, 2H), 2.73-2.88 (m, 8H), 3.12 (m, 1H), 4.17 (m, 2H), 5.27-5.46 (m, 10H); MS (Cl(CH$_4$)): 459 [M+C$_3$H$_5$]$^+$, 447 [M+C$_2$H$_5$]$^+$, 419 [M+H]$^+$, 373 [M−OEt]$^+$, 345 [M−CO$_2$Et]$^+$, 303 [R−S].$^+$.

Example 14

Preparation of 2-((5Z,8Z,11Z,14Z,17Z)-icosa-5,8,11,14,17-pentaenylthio)butanoic acid (10)

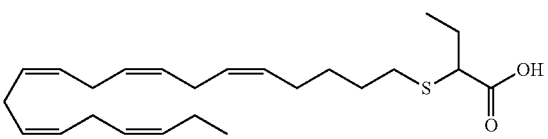 [SMILES: CC/C=C\C/C=C\C/C=C\C/C=C\C/C=C\CCCCSC(CC)C(=O)O]

Ethyl 2-((5Z,8Z,11Z,14Z,17Z)-icosa-5,8,11,14,17-pentaenylthio)butanoate (209 mg, 0.50 mmol) was dissolved in ethanol (2.5 mL) and added to a solution of LiOH×H$_2$O (168 mg, 4.0 mmol) in water (2.5 mL). The resulting turbid solution was stirred at 70° C. under inert atmosphere for 2 hours, cooled and added water (10 mL) and 1 M HCl (5 mL) to pH=1-2. The mixture was extracted with heptane (2×20 mL) and diethyl ether (20 mL). The combined organic extracts were dried (MgSO$_4$), filtered and concentrated under reduced pressure to give 154 mg of the title compound as crude oil. Purification by flash chromatography on silica gel using gradient elution (starting with pure heptane and increasing stepwise to heptane:EtOAc (with 5% HOAc) 80:20) afforded 151 mg (77% yield) of the title compound as oil.

$^1$H-NMR (300 MHz, CDCl$_3$): δ 0.95 (t, 3H), 1.02 (t, 3H), 1.46 (m, 2H), 1.52-1.78 (m, 3H), 1.90 (m, 1H), 2.05 (m, 4H), 2.63 (m, 2H), 2.75-2.90 (m, 8H), 3.14 (t, 1H) (m, 1H), 4.17 (m, 2H), 5.27-5.46 (m, 10H).

Example 15

Preparation of (S)-2-((5Z,8Z,11Z,14Z,17Z)-icosa-5,8,11,14,17-pentaenylthio)butanoic acid (34)

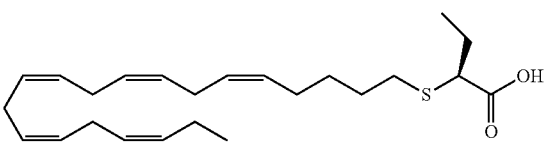 [SMILES: CC/C=C\C/C=C\C/C=C\C/C=C\C/C=C\CCCCS[C@@H](CC)C(=O)O]

Hydrogen peroxide (30% in water, 0.71 mL, 6.91 mmol) and lithium hydroxide monohydrate (0.15 g, 3.46 mmol) was added to a solution of (4S,5R)-3-((S)-2-((5Z,8Z,11Z,14Z,17Z)-icosa-5,8,11,14,17-pentaenylthio)butanoyl)-4-methyl-5-phenyloxazolidin-2-one (0.95 g, 1.73 mmol) in tetrahydrofuran (12 mL) and water (4 mL) held at 0° C. under nitrogen. The reaction mixture was stirred at 0° C. for 30 minutes. 10% Na$_2$SO$_3$ $_{(aq)}$ (30 mL) was added, the pH was adjusted to ~2 with 5M HCl and the mixture was extracted twice with heptane (30 mL). The combined organic extract was dried (Na$_2$SO$_4$), filtered and concentrated. The residue was subjected to flash chromatography on silica gel using increasingly polar mixtures of heptane and ethyl acetate (98:8→1:1) as eluent. Concentration of the appropriate fractions afforded 0.15 g (17% yield) of the title product as an oil.

$^1$H-NMR (300 MHz, CDCl$_3$): δ 1.00 (t, 3H), 1.07 (t, 3H), 1.46 (m, 2H), 1.60-1.75 (m, 3H), 1.85 (m, 1H), 2.10 (m, 4H),

Example 16

Preparation of (R)-2-((5Z,8Z,11Z,14Z,17Z)-icosa-5,8,11,14,17-pentaenylthio)butanoic acid (35)

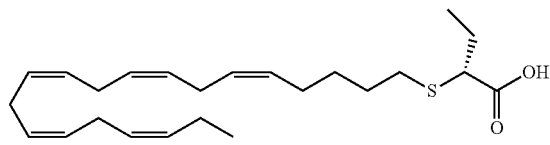 [SMILES: CC/C=C\C/C=C\C/C=C\C/C=C\C/C=C\CCCCS[C@H](CC)C(=O)O]

Hydrogen peroxide (30% in water, 1.04 mL, 10.2 mmol) and lithium hydroxide monohydrate (0.21 g, 5.09 mmol) was added to a solution of (4S,5R)-3-((R)-2-((5Z,8Z,11Z,14Z,17Z)-icosa-5,8,11,14,17-pentaenylthio)butanoyl)-4-methyl-5-phenyloxazolidin-2-one (1.40 g, 2.55 mmol) in tetrahydrofuran (15 mL) and water (5 mL) held at 0° C. under nitrogen. The reaction mixture was stirred at 0° C. for 45 minutes. 10% $Na_2SO_{3\,(aq)}$ (35 mL) was added, pH was adjusted to ~2 with 5M HCl and the mixture was extracted twice with heptane (35 mL). The combined organic extract was dried ($Na_2SO_4$), filtered and concentrated. The residue was subjected to flash chromatography on silica gel using increasingly polar mixtures of heptane and ethyl acetate (98:8→1:1) as eluent. Concentration of the appropriate fractions afforded 0.17 g (22% yield) of the title product as an oil. $^1$H-NMR (300 MHz, CDCl$_3$): δ 1.00 (t, 3H), 1.07 (t, 3H), 1.46 (m, 2H), 1.60-1.75 (m, 3H), 1.85 (m, 1H), 2.10 (m, 4H), 2.66 (m, 2H), 2.80-2.90 (m, 8H), 3.21 (t, 1H), 5.35-5.45 (m, 10H); MS (electrospray): 389.3 [M–H]$^-$; [α]$_D$+50° (c=0.14, ethanol).

Example 17

Preparation of ethyl 2-((5Z,8Z,11Z,14Z,17Z)-icosa-5,8,11,14,17-pentaenylthio)-2-methylpropanoate (36)

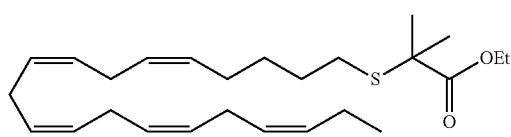

To a solution of (5Z,8Z,11Z,14Z,17Z)-icosa-5,8,11,14,17-pentaene-1-thiol (305 mg, 1.00 mmol) in dry DMF (10 mL) at 0° C. under inert atmosphere was added NaH (60% in mineral oil, 44 mg, 1.1 mmol). After fifteen minutes ethyl 2-bromo-2-methylbutyrate (154 μL, 1.05 mmol) was added and the mixture was stirred for 1.5 hour at 0° C. The reaction mixture was quenched by addition of sat. aq. NH$_4$Cl (20 mL). Water (20 mL) and heptane (50 mL) were added and the phases were separated. The water phase was extracted with heptane (2×25 mL). The combined organics were washed with water (25 mL) and brine (2×25 mL), dried (MgSO$_4$), filtered and evaporated to give 377 mg of the title compound as a crude oil. Purification by flash chromatography on silica gel using isocratic elution (heptane:EtOAc 98:2) afforded 307 mg (77% yield) of the title compound as oil.

$^1$H-NMR (300 MHz, CDCl$_3$): δ 0.95 (t, 3H), 1.28 (t, 3H), 1.42 (m, 2H), 1.48 (s, 6H), 1.54 (m, 2H), 2.06 (m, 4H), 2.58 (m, 2H), 2.71-2.85 (m, 8H), 4.15 (m, 2H), 5.22-5.48 (m, 10H); MS (Cl(CH$_4$)): 459 [M+C$_3$H$_5$]$^+$, 447 [M+C$_2$H$_5$]$^+$, 419 [M+H]$^+$, 373 [M–OEt]$^+$, 345 [M–CO$_2$Et]$^+$, 303 [R–S].$^+$.

Example 18

Preparation of 2-((5Z,8Z,11Z,14Z,17Z)-icosa-5,8,11,14,17-pentaenylthio)-2-methylpropanoic acid (11)

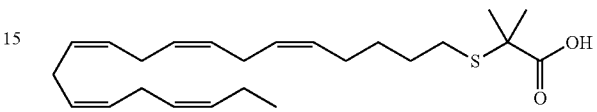

Ethyl 2-((5Z,8Z,11Z,14Z,17Z)-icosa-5,8,11,14,17-pentaenylthio)-2-methylpropanoate (209 mg, 0.50 mmol) was dissolved in ethanol (2.5 mL) and added to a solution of LiOH×H$_2$O (168 mg, 4.0 mmol) in water (2.5 mL). The resulting turbid solution was stirred at 70° C. under inert atmosphere for 2 hours, cooled and added water (10 mL) and 1 M HCl (5 mL) to pH=1-2. The mixture was extracted three times with heptane (3×20 mL). The combined organic extracts were dried (MgSO$_4$), filtered and concentrated under reduced pressure to give 101 mg of the title compound as crude oil. Purification by flash chromatography on silica gel using gradient elution (starting with pure heptane and increasing stepwise to heptane:EtOAc (with 5% HOAc) 80:20) afforded 78 mg (40%) of the title compound as oil.

$^1$H-NMR (300 MHz, CDCl$_3$): δ 0.95 (t, 3H), 1.35-1.66 (m, 4H), 1.50 (s, 6H), 2.07 (m, 4H), 2.63 (t, 3H), 2.70-2.92 (m, 8H), 5.13-5.50 (m, 10H).

Example 19

Preparation of ethyl 1-((5Z,8Z,11Z,14Z,17Z)-icosa-5,8,11,14,17-pentaenylthio)cyclobutanecarboxylate (37)

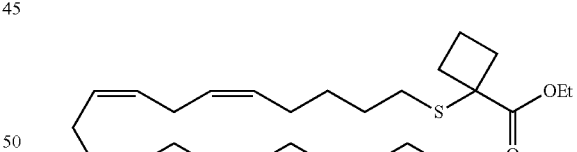

To a solution of (5Z,8Z,11Z,14Z,17Z)-icosa-5,8,11,14,17-pentaene-1-thiol (305 mg, 1.00 mmol) in dry DMF (10 mL) at 0° C. under inert atmosphere was added NaH (60% in mineral oil, 44 mg, 1.1 mmol). After fifteen minutes ethyl 2-bromo-cyclobutane carboxylate (170 μL, 1.05 mmol) was added and the mixture was stirred for 1.5 hour at 0° C. The reaction was quenched by addition of sat. aq. NH$_4$Cl (20 mL). Heptane (50 mL) was added, and the phases were separated. The water phase was extracted with heptane (2×25 mL). The combined organics were washed with water (25 mL) and brine (25 mL), dried (MgSO$_4$), filtered and evaporated to give 409 mg of the title compound as a crude oil. Purification by flash chromatography on silica gel using isocratic elution (heptane:acetone 98:2) afforded 243 mg (56% yield) of the title compound as oil.

$^1$H-NMR (300 MHz, CDCl$_3$): δ 0.95 (t, 3H), 1.27 (t, 3H), 1.42 (d, 3H), 1.54 (m, 2H), 1.84 (m, 1H), 1.96-2.23 (m, 7H), 2.51 (m, 2H), 2.60 (m, 2H), 2.73-2.90 (m, 8H), 4.18 (m, 2H), 5.23-5.43 (m, 10H); MS (Cl(CH$_4$)): 471 [M+C$_3$H$_5$]$^+$, 459 [M+C$_2$H$_5$]$^+$, 431 [M+H]$^+$, 385 [M–OEt]$^+$, 357 [M–CO$_2$Et]$^+$, 303 [R–S].$^+$.

Example 20

Preparation of 2-ethyl-2-((5Z,8Z,11Z,14Z,17Z)-icosa-5,8,11,14,17-pentaenylthio)butanoic acid (12)

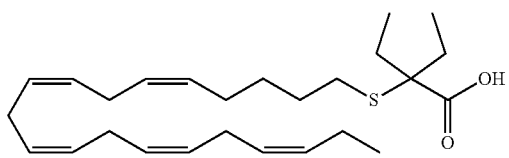 [SMILES: CC/C=C\C/C=C\C/C=C\C/C=C\C/C=C\CCCCSC(CC)(CC)C(=O)O]

NaOEt (21 wt. % in EtOH, 0.37 mL, 0.98 mmol) was added dropwise to a solution of 2-mercapto-2-ethyl butyric acid (0.08 g, 0.49 mmol) in dry EtOH (7 mL) held at 0° C. under inert atmosphere. The resulting mixture was stirred at 0° C. for 30 minutes before a solution of (5Z,8Z,11Z,14Z,17Z)-icosa-5,8,11,14,17-pentaenyl methanesulfonate (0.15 g, 0.41 mmol) in dry EtOH (3 mL) was added dropwise. The resulting turbid mixture was stirred at ambient temperature for 24 hours, poured into NH4Cl (sat.)(aq.) (15 mL), added 3M HCl to pH ~2 before extracted twice with EtOAc (2×20 mL). The combined organic extracts were washed with brine (10 mL), dried (MgSO4), filtrated and evaporated in vacuo. The residue was purified by flash chromatography on silica gel using a gradient of 10-25% ethyl acetate in heptane as eluent. Concentration of the appropriate fractions afforded 0.12 g (70% yield) of the title compound as oil.

1H-NMR (300 MHz, CDCl$_3$): δ 0.88-1.02 (m, 9H), 1.45-1.58 (2×m, 4H), 1.72 (m, 2H), 1.82 (m, 2H) 2.09 (m, 4H), 2.53 (t, 2H), 2.76-2.86 (m, 8H), 5.29-5.39 (m, 10H. MS (electrospray): 417.3 [M–H]–;

Example 21

Preparation of ethyl ethyl 2-((5Z,8Z,11Z,14Z,17Z)-icosa-5,8,11,14,17-pentaenylthio)-2-phenylacetate (38)

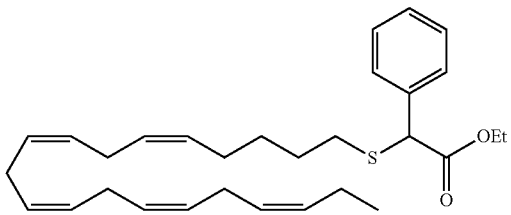 [SMILES: CC/C=C\C/C=C\C/C=C\C/C=C\C/C=C\CCCCSC(C(=O)OCC)c1ccccc1]

To a solution of (5Z,8Z,11Z,14Z,17Z)-icosa-5,8,11,14,17-pentaene-1-thiol (305 mg, 1.00 mmol) in dry DMF (10 mL) at 0° C. under inert atmosphere was added NaH (60% in mineral oil, 44 mg, 1.1 mmol). After fifteen minutes. ethyl 2-bromo-2-phenyl acetate (255 mg, 1.05 mmol) was added and the mixture stirred for 1.5 hour at 0° C. The reaction mixture was quenched by addition of sat. aq. NH$_4$Cl (25 mL). Heptane (50 mL) was added and the phases were separated. The water phase was extracted with heptane (2×25 mL). The combined organics were washed with water (25 mL) and brine (25 mL), dried (MgSO$_4$), filtered and evaporated to give 453 mg of title compound as crude oil. Purification by flash chromatography on silica gel using isocratic elution (heptane:EtOAc 98:2) afforded 177 mg (38% yield) of the title compound as oil.

$^1$H-NMR (300 MHz, CDCl$_3$): δ 0.95 (t, 3H), 1.24 (t, 3H), 1.41 (m, 2H), 1.56 (m, 2H), 2.05 (m, 2H), 2.51 (m, 2H), 2.60 (m, 2H), 2.67-2.92 (m, 8H), 4.17 (m, 2H), 4.53 (s, 1H), 5.21-5.46 (m, 10H), 7.27-7.35 (m, 3H), 7.43-7.46 (m, 2H); MS (Cl(CH$_4$)): 507 [M+C$_3$H$_5$]$^+$, 495 [M+C$_2$H$_5$]$^+$, 467 [M+H]$^+$, 421 [M–OEt]$^+$, 393 [M–CO$_2$Et]$^+$, 303 [R–S].$^+$.

Biological Testing

Example 22

Evaluation of PPAR Activation In-Vitro

The assay was carried out in-vitro in three stable reporter cell lines, PPARα, PPARδ or PPARγ, expressing respectively a chimeric protein containing the ligand binding domain (LBD) of human PPARα, human PPARδ or human PPARγ fused to the yeast transactivator GAL4 DNA binding domain (DBD).

The luciferase (Luc) reporter gene is driven by a pentamer of the GAL4 recognition sequence in front of a β-globin promoter. The use of GAL4-PPARα, GAL4-PPARδ and GAL4-PPARγ chimeric receptors allows for elimination of background activity from endogenous receptors and quantitation of relative activity across the three PPAR subtypes with the same reporter gene.

Two unsubstituted reference substances, Reference 1 and 2, and five test substances, (7), (10), (11), (24) and (25) were tested in a concentration of 10 μM. The structural formulae of the tested substances are as show below:

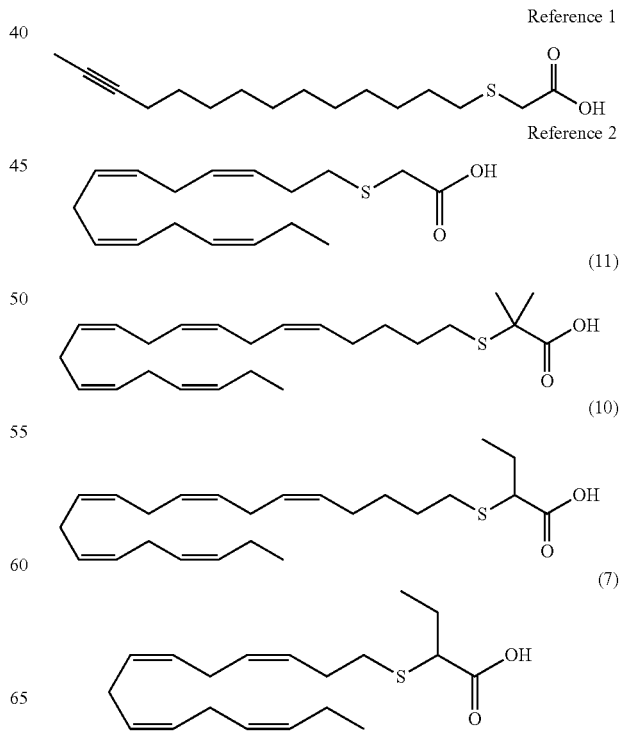

-continued

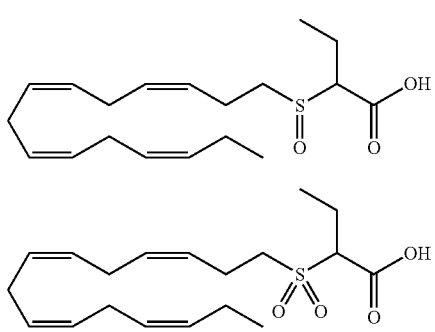

The PPAR selectivity of the substances was determined by comparison to known drug references (1 µM GW7647 for PPARα, 1 µM L-165041 for PPARδ and 1 µM BRL49653 for PPARγ) set of 100% activity.

The results are presented in FIG. 1.

Example 23

Evaluation of PPARα Activation In-Vitro
(Concentration Response Data)

The assay was carried out in-vitro using mammalian-one-hybrid assays (M1H) comprising GAL4-DNA binding domain-PPARα-LBD fusion constructs in conjunction with 5×GAL4-sites driven *Photinus pyralis* luciferase reporter construct in transiently transfected HEK293 cells.

Compound (12) and positive control (GW7647) were tested at different concentrations. The results are presented in Table 1.

TABLE 1

| | PPARα | |
| Compound | EC50 (nM) | Efficacy (%) |
| --- | --- | --- |
| GW7647 | 0.45 | 100 |
| (12) | 286 | 84 |

Example 24

Evaluation of the Effects on Lipid Metabolism
In-Vivo in a Dyslipidemic Model

APOE*3Leiden Transgenic Mice

This animal model has proven to be representative for the human situation regarding plasma lipoprotein levels, lipoprotein profiles, its responsiveness to hypolipidemic drugs (like statins, fibrates etc.) and nutrition. In addition, depending on the level of plasma cholesterol APOE*3Leiden mice develop atherosclerotic lesions in the aorta resembling those found in humans with respect to cellular composition and morphological and immunohistochemical characteristics.

Female APOE*3Leiden mice were put on a semi-synthetic Western-type diet (WTD, 15% cocoa butter, 40% sucrose and 0.25% cholesterol; all w/w). With this diet the plasma cholesterol level reached mildly elevated levels of about 12-15 mmol/l. After a 4 weeks run-in period the mice were sub-divided into groups of 10 mice each, matched for plasma cholesterol, triglycerides and body weight (t=0).

The test substances were administered orally as admix to the Western-type diet. To facilitate the mixing of the compounds sunflower oil was added to a total oil volume of 10 mL/kg diet.

After three weeks of treatment (t=3 weeks) mice were fasted overnight (o/n) and blood samples were taken to measure plasma ketone bodies and free fatty acids. At t=0 and 4 weeks blood samples were taken after a 4 hour-fast period to measure plasma cholesterol and triglycerides.

Two unsubstituted reference substances, Reference 3 and 2, and three test substances, (7), (10) and (12), were dosed at 0.3 mmol/kg bw/day. The structural formulae of the tested substances are as show below:

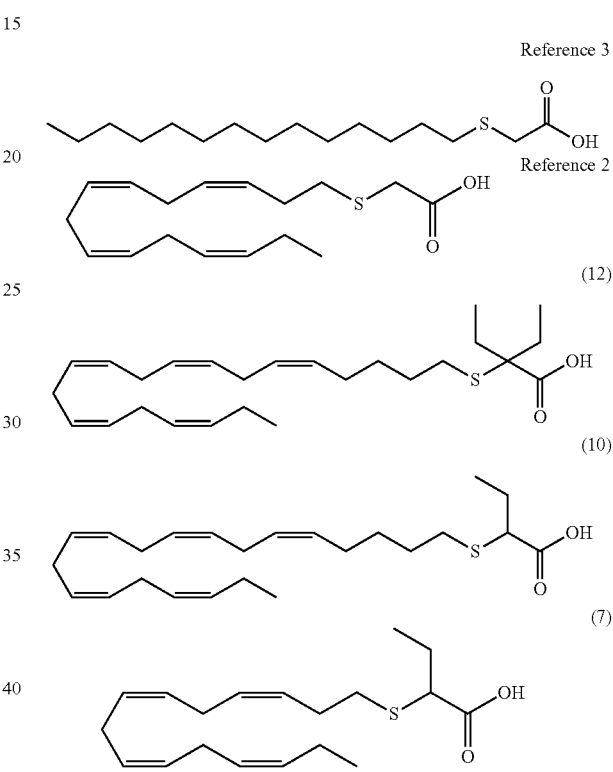

Figure 2:
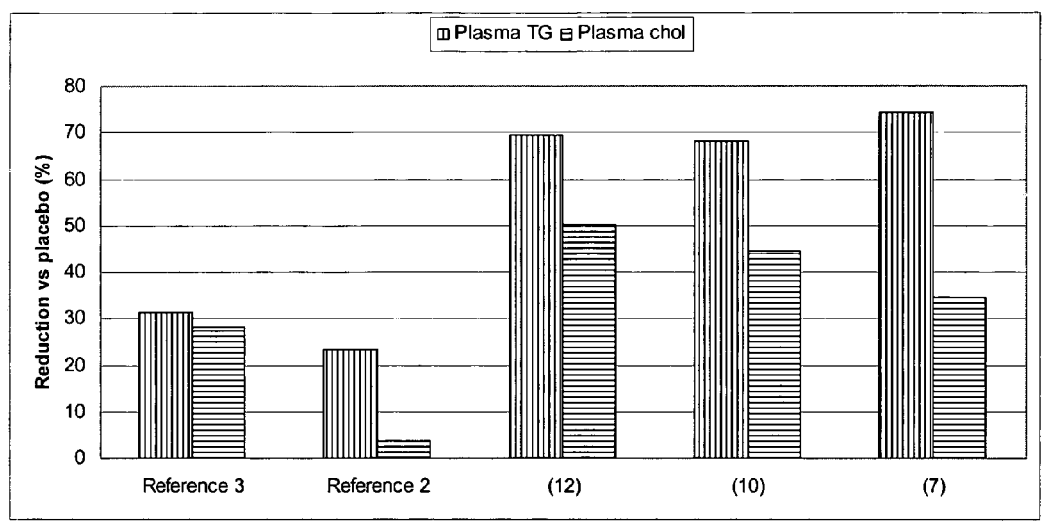
FIG. 2 Plasma triglyceride levels and plasma cholesterol levels in APOE*3Leiden mice after administration of compounds according to the present disclosure and unsubstituted reference substances.
Figure 3:
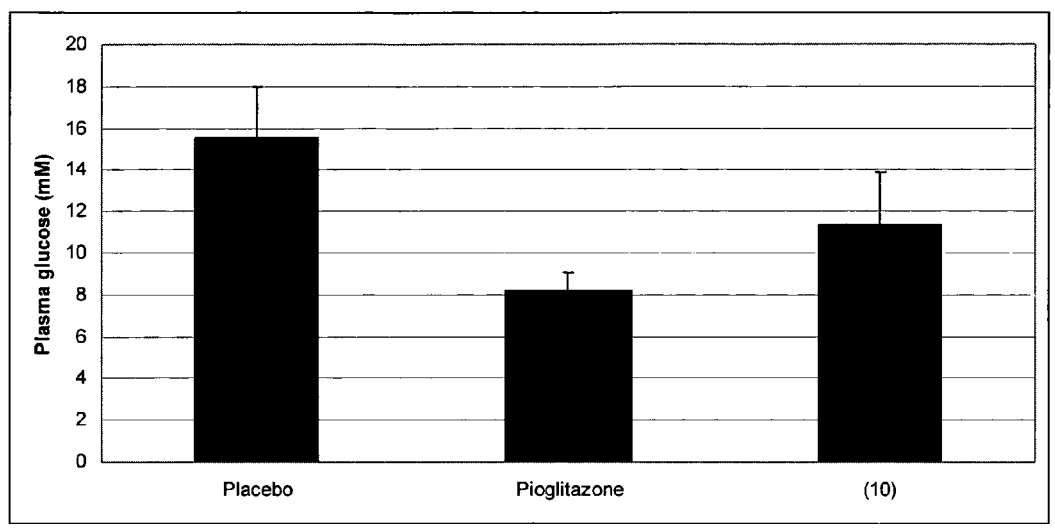
FIG. 3: Plasma glucose levels in ob/ob mice after administration of 2-((5Z,8Z,11Z,14Z,17Z)-icosa-5,8,11,14,17-pentaenylthio)butanoic acid, pioglitazone, and a placebo.
Figure 4:
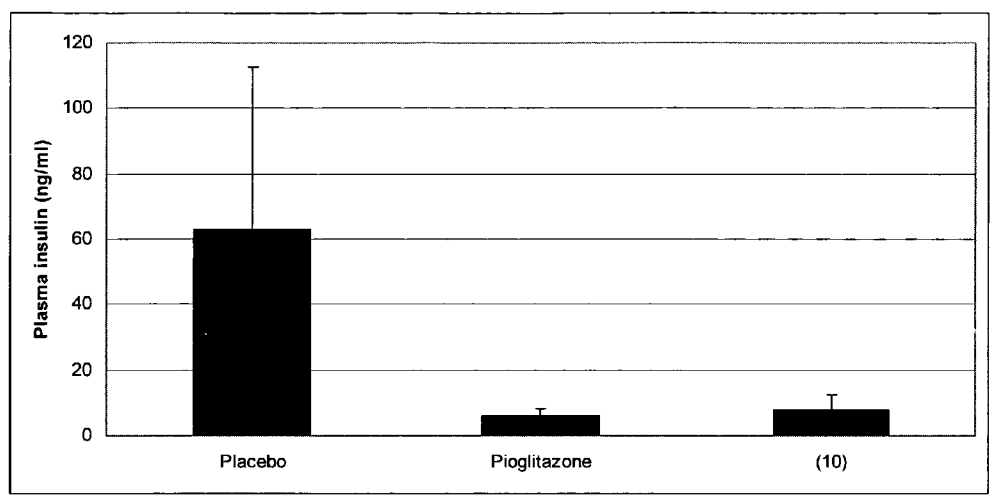
FIG. 4: Plasma insulin levels in ob/ob mice after administration of 2-((5Z,8Z,11Z,14Z,17Z)-icosa-5,8,11,14,17-pentaenylthio)butanoic acid, pioglitazone, and a placebo.
Figure 5:
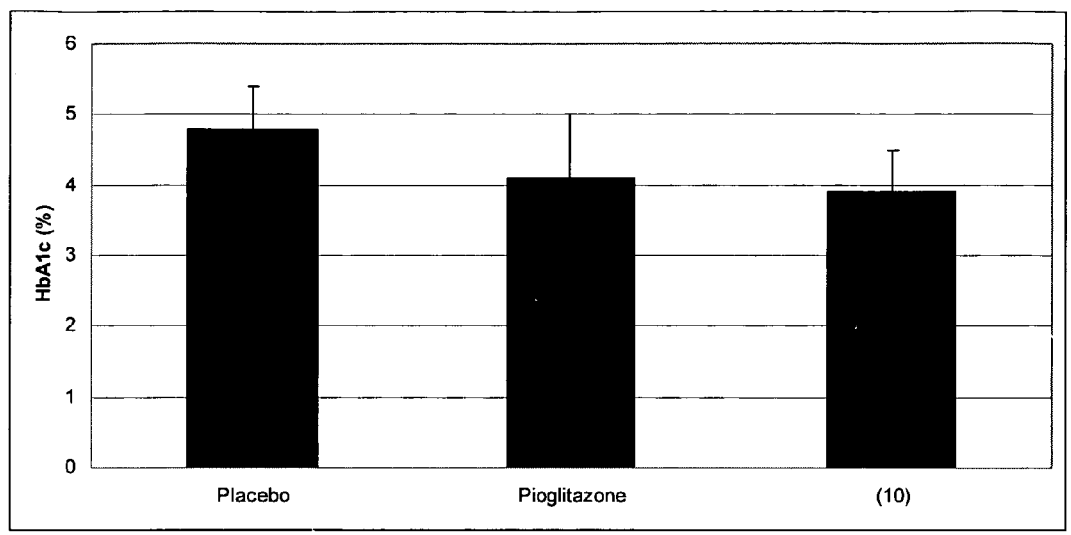
FIG. 5: Whole blood HbA1c levels in ob/ob mice after adminstration of 2-((5Z,8Z,11Z,14Z,17Z)-icosa-5,8,11,14,17-pentaenylthio)butanoic acid, pioglitazone, and a placebo.
Figure 6:
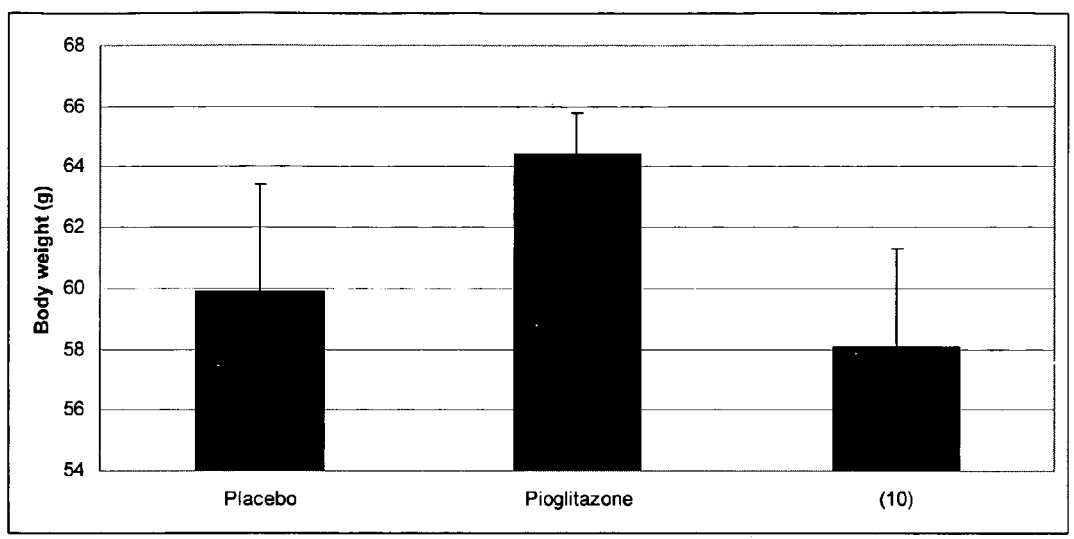
FIG. 6: Body weight differences in ob/ob mice after adminstration of 2-((5Z,8Z,11z,14Z,17Z)-icosa-5,8,11,14,17-pentaenylthio)butanoic acid, pioglitazone, and a placebo.

The results are shown in FIG. 2.

Example 25

Evaluation of the Effects on Glucose Metabolism in
a Diabetes Type-II Model

Male ob/ob Mice

Ob/ob mice can be used as a model for type II diabetes. The mice are homozygous for the obese spontaneous mutation (Lep$^{ob}$) leading to leptin deficiency. In addition to obesity (ob/ob mice may reach three times the normal body weight of wild type controls), ob/ob mice exhibit a diabetes type II-like syndrome of hyperglycemia, glucose intolerance, elevated plasma insulin, infertility, impaired wound healing, and an increase in hormone production from both pituitary and adrenal glands.

Male ob/ob mice were put on a normal low-fat diet for a few weeks for acclimatization. After the acclimatization period the mice were sub-divided into three groups of 10 mice each, matched for body weight, plasma glucose and insulin (t=0).

All compounds were administered orally as admix to AM II diet. To facilitate the mixing of the compounds, sunflower oil was added to a total oil volume of 10 ml/kg diet.

At t=0, 2 and 4 weeks body weight and food intake was measured. At t=0, 2 and 4 weeks blood samples were taken after a 4 hour-fast period to measure whole blood HbA1c and plasma glucose, insulin, cholesterol and triglycerides.

Pioglitazone was used as reference (15 mg/kg bw/day). Compound (10) was dosed at 0.6 mmol/kg bw/day. The results (t=4) are shown in FIGS. 3-6.

The invention claimed is:
1. A lipid compound of formula (I):

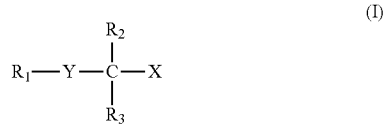

wherein
- $R_1$ is chosen from a $C_{10}$-$C_{22}$ alkenyl group having 3-6 methylene interrupted double bonds in Z configuration and a $C_{10}$-$C_{22}$ alkynyl group having 1-6 triple bonds;
- $R_2$ and $R_3$ are the same or different and each are independently chosen from a hydrogen atom, a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group, or an alkylamino group, provided that $R_2$ and $R_3$ are not both a hydrogen atom; or
- $R_2$ and $R_3$ are connected in order to form a cycloalkane;
- Y is chosen from sulphur, sulfoxide, and sulfone;
- X is a carboxylic acid or a derivative thereof, wherein the derivative is a carboxylic ester, or a carboxamide, a monoglyceride, a diglyceride, a triglyceride or a phospholipid;

or a pharmaceutically acceptable salt thereof, with the proviso that the compound of formula (I) is not 2-((5Z,8Z,11Z,14Z,17Z)-icosa-5,8,11,14,17-pentaenylthio) butanoic acid.

2. The lipid compound according to claim 1, wherein $R_2$ and $R_3$ each are independently chosen from a hydrogen atom, an alkyl group, an alkoxy group, or an aryl group; or $R_2$ and $R_3$ are connected in order to form a cycloalkane.

3. The lipid compound according to claim 2, wherein $R_2$ and $R_3$ each are independently chosen from a hydrogen atom, an alkyl group, a methoxy group, or an ethoxy group.

4. The lipid compound according to claim 2, wherein $R_2$ and $R_3$ each are independently chosen from a hydrogen atom, an ethyl group, a methoxy group, an ethoxy group, or a phenyl group; or $R_2$ and $R_3$ are connected to form a cyclobutane group.

5. The lipid compound according to claim 1, wherein one of $R_2$ and $R_3$ is a hydrogen atom and the other one is chosen from a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group, or an alkylamino group.

6. The lipid compound according to claim 1, wherein $R_2$ and $R_3$ are the same or different and each are independently chosen from a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, or an amino group.

7. The lipid compound according to claim 6, wherein $R_2$ and $R_3$ are alkyl groups.

8. The lipid compound according to claim 7, wherein $R_2$ and $R_3$ are the same or different and each are independently chosen from a methyl group, an ethyl group, an n-propyl group, or an isopropyl group.

9. The lipid compound according to claim 7, wherein $R_2$ and $R_3$ are ethyl groups.

10. The lipid compound according to claim 1, wherein $R_1$ is a $C_{10}$-$C_{22}$ alkenyl group with 3-6 methylene interrupted double bonds in Z configuration.

11. The lipid compound according to claim 10, wherein said lipid compound is derived from a polyunsaturated fatty acid.

12. The lipid compound according to claim 10, wherein $R_1$ is a $C_{10}$-$C_{22}$ alkenyl group having 3-6 double bonds.

13. The lipid compound according to claim 1, wherein $R_1$ is a $C_{14}$-$C_{22}$ alkenyl group having 3-6 methylene interrupted double bonds in Z configuration, wherein the first double bond of the at least one double bond is located at the third carbon-carbon bond from the omega (w) end of the carbon chain.

14. The lipid compound according to claim 13, wherein $R_1$ is a $C_{14}$-$C_{22}$ alkenyl group having 5 or 6 double bonds.

15. The lipid compound according to claim 1, wherein $R_1$ is a $C_{10}$-$C_{22}$ alkynyl group, said lipid compound being derived from lipids comprising 1-6 triple bonds.

16. The lipid compound according to claim 1, wherein Y is sulfur.

17. The lipid compound according to claim 1, wherein Y is sulfoxide.

18. The lipid compound according to claim 1, wherein Y is sulfone.

19. The lipid compound according to claim 1, wherein X is a carboxylic acid or a derivative thereof in the form of an ester.

20. The lipid compound according to claim 19, wherein X is a carboxylic acid.

21. The lipid compound according to claim 1, wherein
- $R_2$ and $R_3$ are the same or different and each are independently chosen from a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, or an amino group; and
- X is a carboxylic acid.

22. The lipid compound according to claim 21, wherein $R_2$ and $R_3$ are alkyl groups.

23. The lipid compound according to claim 1, wherein said salt of said lipid compound comprises a monovalent cation, a divalent cation, or a polyvalent cation.

24. The lipid compound according to claim 1, wherein said lipid compound comprises a mixture of diastereomeric isomers or is in racemic form.

25. The lipid compound according to claim 24, in the form of a diastereomer or an enantiomer.

26. The lipid compound according to claim 24, in the form of its R stereoisomer.

27. The lipid compound according to claim 24, in the form of its S stereoisomer.

28. The lipid compound according to claim 1, wherein said compound is:

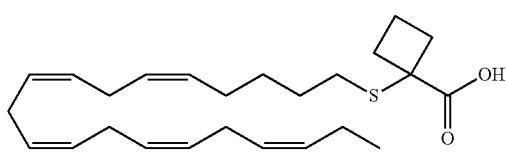 [SMILES: CC/C=C\C/C=C\C/C=C\C/C=C\C/C=C\CCCCSC1(C(=O)O)CCC1]

1-((5Z,8Z,11Z,14Z,17Z)-icosa-5,8,11,14,17-pentaenylthio)cyclobutanecarboxylic acid;

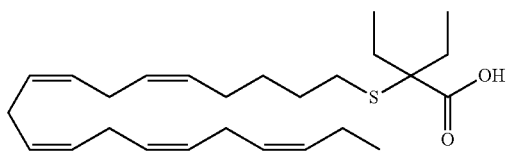 [SMILES: CC/C=C\C/C=C\C/C=C\C/C=C\C/C=C\CCCCSC(CC)(CC)C(=O)O]

2-ethyl-2-((5Z,8Z,11Z,14Z,17Z)-icosa-5,8,11,14,17-pentaenylthio)butanoic acid;

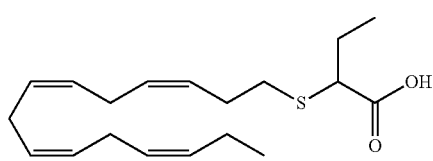 [SMILES: CC/C=C\C/C=C\C/C=C\C/C=C\CCSC(CC)C(=O)O]

2-((3Z,6Z,9Z,12Z)-pentadeca-3,6,9,12-tetraenylthio)butanoic acid;

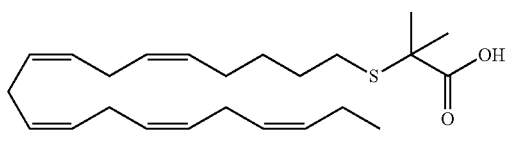 [SMILES: CC/C=C\C/C=C\C/C=C\C/C=C\C/C=C\CCCCSC(C)(C)C(=O)O]

2-((5Z,8Z,11Z,14Z,17Z)-icosa-5,8,11,14,17-pentaenylthio)-2-methylpropanoic acid;

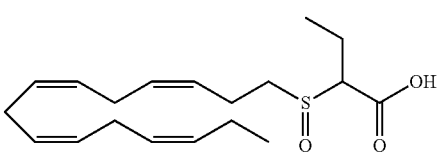

2-((3Z,6Z,9Z,12Z)-pentadeca-3,6,9,12-tetraenylsulfinyl) butanoic acid;

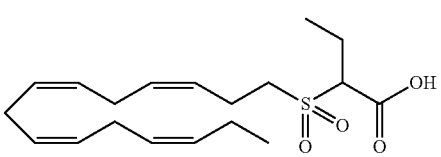 [SMILES: CC/C=C\C/C=C\C/C=C\C/C=C\CCS(=O)(=O)C(CC)C(=O)O]

2-((3Z,6Z,9Z,12Z)-pentadeca-3,6,9,12-tetraenylsulfonyl) butanoic acid;

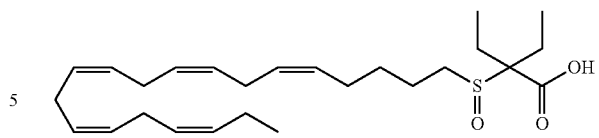

2-ethyl-2-((5Z,8Z,11Z,14Z,17Z)-icosa-5,8,11,14,17-pentaenylsulfinyl)butanoic acid; or

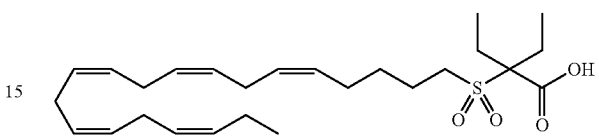

2-ethyl-2-((5Z,8Z,11Z,14Z,17Z)-icosa-5,8,11,14,17-pentaenylsulfonyl)butanoic acid.

29. The lipid compound according to claim 1, wherein
X is a carboxylic acid or a derivative thereof, wherein the derivative is a monoglyceride, a diglyceride, a triglyceride, a phospholipid, a carboxylic ester, or a carboxamide; and
Y is sulphur.

30. The lipid compound according to claim 1, wherein
$R_1$ is a $C_{10}$-$C_{22}$ alkenyl group having 3-6 methylene interrupted double bonds in Z configuration, said lipid compound being derived from a polyunsaturated fatty acid;
X is a carboxylic acid or a derivative thereof, wherein the derivative is a monoglyceride, a diglyceride, a triglyceride, a phospholipid, a carboxylic ester, or a carboxamide; and
Y is sulphur.

31. The lipid compound according to claim 1, wherein
$R_1$ is a $C_{10}$-$C_{22}$ alkynyl group, said lipid compound being derived from lipids containing 1-6 triple bonds; and
X is a carboxylic acid or a derivative thereof, wherein the derivative is a monoglyceride, a diglyceride, a triglyceride, a phospholipid, a carboxylic ester, or a carboxamide; and
Y is sulphur.

32. The lipid compound according to claim 1, wherein
$R_1$ is chosen from a $C_{10}$-$C_{22}$ alkenyl group having 3-6 methylene interrupted double bonds in Z configuration or a $C_{10}$-$C_{22}$ alkynyl group having 1-6 triple bonds;
X is a carboxylic acid or a derivative thereof, wherein the derivative is a monoglyceride, a diglyceride, a triglycerde, a phospholipid, a carboxylic ester, or a carboxamide; and
Y is sulfoxide or sulfone.

33. A food supplement composition comprising at least one lipid compound according to claim 1.

34. A pharmaceutical composition comprising at least one lipid compound according to claim 1.

35. The pharmaceutical composition according to claim 34, further comprising at least one pharmaceutically acceptable carrier, excipient, diluent, or any combination thereof.

36. The pharmaceutical composition according to claim 34, further comprising at least one pharmaceutically acceptable antioxidant.

37. The pharmaceutical composition according to claim 36, wherein said at least one pharmaceutically acceptable antioxidant is tocopherol.

38. The pharmaceutical composition according to claim 34, formulated for oral administration.

39. The pharmaceutical composition according to claim 38, in the form of a capsule or a tablet.

40. The pharmaceutical composition according to claim 34, formulated to provide a daily dosage ranging from 1 mg to 10 g of said lipid compound.

41. The pharmaceutical composition according to claim 40, formulated to provide a daily dosage ranging from 50 mg to 1 g of said lipid compound.

42. The pharmaceutical composition according to claim 41, formulated to provide a daily dosage ranging from 50 mg to 200 mg of said lipid compound.

43. A lipid composition comprising at least one lipid compound according to claim 1.

44. The lipid composition according to claim 43, wherein said at least one lipid compound comprises at least 60% by weight of said lipid composition.

45. The lipid composition according to claim 43, wherein said at least one lipid compound comprises at least 80% by weight of said lipid composition.

46. The lipid composition according to claim 43, further comprising at least one pharmaceutically acceptable antioxidant.

47. The lipid composition according to claim 46, wherein said at least one pharmaceutically acceptable antioxidant is tocopherol.

48. A method for activation or modulation of at least one human peroxisome proliferator-activated receptor (PPAR) isoform chosen from α, γ, or δ in a mammal, the method comprising administering to said mammal a pharmaceutically active amount of at least one lipid compound according to claim 1.

49. The method according to claim 48, wherein said at least one lipid compound is a PPAR pan-agonist or modulator.

50. A method for the treatment of a dyslipidemic condition in a mammal in need thereof, the method comprising administering to said mammal a pharmaceutically active amount of at least one lipid compound according to claim 1.

51. The method according to claim 50, wherein said dyslipidemic condition is hypertriglyceridemia (HTG).

52. A method for the treatment of elevated triglyceride levels, LDL cholesterol levels, and VLDL cholesterol levels in a mammal in need thereof, the method comprising administering to said mammal a pharmaceutically active amount of at least one lipid compound according to claim 1.

53. A method for the treatment of obesity or an overweight condition in a mammal in need thereof, the method comprising administering to said mammal a pharmaceutically active amount of at least one lipid compound according to claim 1.

54. A method for reduction of body weight, the method comprising administering to said mammal a pharmaceutically active amount of at least one lipid compound according to claim 1.

55. A method for the treatment of a fatty liver disease in a mammal in need thereof, the method comprising administering to said mammal a pharmaceutically active amount of at least one lipid compound according to claim 1.

56. The method according to claim 55, wherein said fatty liver diesase is non-alcoholic fatty liver disease (NAFLD).

57. A method for the treatment of at least one condition chosen from peripheral insulin resistance and a diabetic condition in a mammal in need thereof, the method comprising administering to said mammal a pharmaceutically active amount of at least one lipid compound according to claim 1.

58. A method for the treatment of type 2 diabetes in a mammal in need thereof, the method comprising administering to said mammal a pharmaceutically active amount of at least one lipid compound according to claim 1.

59. A method for reduction of at least one of plasma insulin, blood glucose, and serum triglycerides in a mammal in need thereof, the method comprising administering to said mammal a pharmaceutically active amount of at least one lipid compound according to claim 1.

60. The lipid compound according to claim 23, wherein the monovalent cation is chosen from $Li^+$, $Na^+$, $K^+$, $NH_4^+$, meglumine, tris(hydroxymethyl)aminomethane, diethylamine, or arginine.

61. The lipid compound according to claim 23, wherein the divalent cation is chosen from $Mg^{2+}$, $Ca^{2+}$, ethylenediamine, or piperazine.

62. The lipid compound according to claim 23, wherein the polyvalent cation is chosen from chitosan.

63. The lipid compound according to claim 28, wherein said compound is

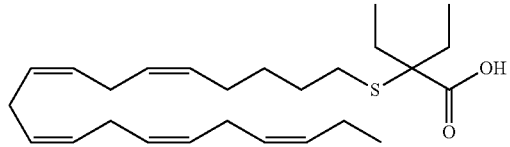

2-ethyl-2-((5Z,8Z,11Z,14Z,17Z)-icosa-5,8,11,14,17-pentaenylthio)butanoic acid.

64. A lipid composition comprising the lipid compound according to claim 63.

65. The lipid composition according to claim 64, wherein the composition is a pharmaceutical composition.

66. The lipid compound of claim 1, wherein the cycloalkane is selected from cyclopropane, cyclobutane, cyclopentane, or cyclohexane.

67. A lipid compound of formula (I):

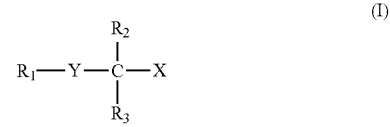

wherein
R$_1$ is chosen from a $C_{10}$-$C_{22}$ alkenyl group having 3-6 methylene interrupted double bonds in Z configuration;
R$_2$ and R$_3$ are the same or different and each are independently chosen from a hydrogen atom, a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group, or an alkylamino group, provided that R$_2$ and R$_3$ are not both a hydrogen atom; or
R$_2$ and R$_3$ are connected in order to form a cycloalkane;
Y is chosen from sulphur, sulfoxide, and sulfone;
X is a carboxylic acid or a derivative thereof, wherein the derivative is a carboxylic ester, or a carboxamide, a monoglyceride, a diglyceride, a triglyceride or a phospholipid;
or a pharmaceutically acceptable salt thereof,
with the proviso that the compound of formula (I) is not 2-((5Z,8Z,11Z,14Z,17Z)-icosa-5,8,11,14,17-pentaenylthio)butanoic acid.

68. A lipid compound of formula (I):

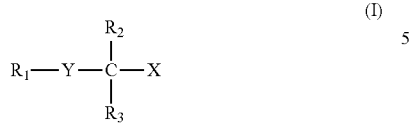

wherein
- R$_1$ is chosen from a C$_{10}$-C$_{22}$ alkenyl group having 3-6 methylene interrupted double bonds in Z configuration or a C$_{18}$-C$_{22}$ alkynyl group having 1-6 triple bonds;
- R$_2$ and R$_3$ are the same or different and each are independently chosen from a hydrogen atom, a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group, or an alkylamino group, provided that R$_2$ and R$_3$ are not both a hydrogen atom; or
- R$_2$ and R$_3$ are connected in order to form a cycloalkane;
- Y is chosen from sulphur, sulfoxide, and sulfone;
- X is a carboxylic acid or a derivative thereof, wherein the derivative is a carboxylic ester, or a carboxamide, a monoglyceride, a diglyceride, a triglyceride or a phospholipid;

or a pharmaceutically acceptable salt thereof,
with the proviso that the compound of formula (I) is not 2-((5Z,8Z,11Z,14Z,17Z)-icosa-5,8,11,14,17-pentaenylthio)butanoic acid.

69. The lipid compound according to claim 1, wherein X is a carboxamide selected from the group consisting of N-methyl carboxamide, N,N-dimethyl carboxamide, N-ethyl carboxamide, and N,N-diethyl carboxamide.

70. The lipid compound according to claim 67, wherein X is a carboxamide selected from the group consisting of N-methyl carboxamide, N,N-dimethyl carboxamide, N-ethyl carboxamide, and N,N-diethyl carboxamide.

71. The lipid compound according to claim 68, wherein X is a carboxamide selected from the group consisting of N-methyl carboxamide, N,N-dimethyl carboxamide, N-ethyl carboxamide, and N,N-diethyl carboxamide.

* * * * *

UNITED STATES PATENT AND TRADEMARK OFFICE
CERTIFICATE OF CORRECTION

PATENT NO. : 8,759,558 B2
APPLICATION NO. : 13/054212
DATED : June 24, 2014
INVENTOR(S) : Anne Kristin Holmeide et al.

Page 1 of 1

It is certified that error appears in the above-identified patent and that said Letters Patent is hereby corrected as shown below:

In the Claims:

Claim 1, column 41, line 39, "or a carboxamide" should read --a carboxamide--.

Claim 32, column 44, lines 49-51, "a triglycerde" should read --a triglyceride--.

Claim 56, column 45, line 56, "fatty liver diesease" should read --fatty liver disease--.

Claim 67, column 46, line 61, "or a carboxamide" should read --a carboxamide--.

Claim 68, column 48, line 4, "or a carboxamide" should read --a carboxamide--.

Signed and Sealed this
Seventh Day of October, 2014

Michelle K. Lee
*Deputy Director of the United States Patent and Trademark Office*